United States Patent
Okazaki et al.

(10) Patent No.: US 12,275,958 B2
(45) Date of Patent: Apr. 15, 2025

(54) GUT ORGANOID AND METHOD FOR PRODUCING THE SAME

(71) Applicants: DAI NIPPON PRINTING CO., LTD., Tokyo (JP); NATIONAL CENTER FOR CHILD HEALTH AND DEVELOPMENT, Tokyo (JP)

(72) Inventors: Takuya Okazaki, Tokyo (JP); Akihiro Umezawa, Tokyo (JP); Hidenori Akutsu, Tokyo (JP); Hajime Uchida, Tokyo (JP)

(73) Assignees: DAI NIPPON PRINTING CO., LTD., Tokyo (JP); NATIONAL CENTER FOR CHILD HEALTH AND DEVELOPMENT, Tokyo (JP)

( * ) Notice: Subject to any disclaimer, the term of this patent is extended or adjusted under 35 U.S.C. 154(b) by 1227 days.

(21) Appl. No.: 16/713,808

(22) Filed: Dec. 13, 2019

(65) Prior Publication Data

US 2020/0102543 A1 Apr. 2, 2020

Related U.S. Application Data

(63) Continuation of application No. PCT/JP2018/013950, filed on Mar. 30, 2018.

(30) Foreign Application Priority Data

Jun. 13, 2017 (JP) ................... 2017-115952

(51) Int. Cl.
C12N 5/071 (2010.01)
G01N 33/50 (2006.01)

(52) U.S. Cl.
CPC ......... *C12N 5/0697* (2013.01); *C12N 5/0679* (2013.01); *G01N 33/5082* (2013.01); *C12N 2506/02* (2013.01); *C12N 2506/45* (2013.01); *C12N 2513/00* (2013.01)

(58) Field of Classification Search
CPC ............... C12N 5/0697; C12N 5/0679; C12N 2506/02; C12N 2506/45; C12N 2513/00; C12N 2503/04; C12N 15/09; G01N 33/5082; Y02A 50/30

See application file for complete search history.

(56) References Cited

FOREIGN PATENT DOCUMENTS

| EP | 1 970 446 A1 | 9/2008 |
|---|---|---|
| JP | 2006-239169 A | 9/2006 |
| JP | 2014-236716 A | 12/2014 |
| JP | 2015-015943 A | 1/2015 |
| JP | 2017-184749 A | 10/2017 |
| WO | 2006/071911 A2 | 7/2006 |
| WO | 2007/069666 A1 | 6/2007 |
| WO | 2010/143747 A1 | 12/2010 |
| WO | 2014/132933 A1 | 9/2014 |

OTHER PUBLICATIONS

Zhao et al ("A Novel Model of P-Glycoprotein Inhibitor Screening Using Human Small Intestinal Organoids," 2016 Nordic Association for the Publication of BCPT, first published Sep. 22, 2016) (former Nordic Pharmacological Society) (Year: 2016).*
Mawe et al ("Serotonin signaling in the gastrointestinal tract: functions, dysfunctions and therapeutic target;" Nat Rev Gastroenterol Hepatol.Aug. 10, 2013(8);473-486) (Year: 2013).*
Dekkers et al ("A functional CFTR assay using primary cystic fibrosis intestinal organoids;" nature medicine vol. 19 | No. 7 | Jul. 2013) (Year: 2013).*
Groneberg et al ("Intestinal peptide transport: ex vivo uptake studies and localization of peptide carrier PEPT1," Am J Physiol Gastrointest Liver Physiol 281: G697-G704) 2001 (Year: 2001).*
Taipalensuu et al ("Correlation of Gene Expression of Ten Drug Efflux Proteins of the ATP-Binding Cassette Transporter Family in Normal Human Jejunum and in Human Intestinal Epithelial Caco-2 Cell Monolayers," The Journal of Pharmacology and Experimental Therapeutics vol. 299, No. 1, 2001). (Year: 2001).*
Kim et al ("Effects of Histamine on Cultured Interstitial Cells of Cajal in Murine Small Intestine," Korean J Physiol Pharmacol vol. 17: 149-156, Apr. 2013) (Year: 2013).*
Bertaccini et al ("Different mechanisms are responsible for the contractile effects histaminergic compounds on isolated intestinal smooth muscle cells," J Physiology (Paris) (1997) 91: 199-202). (Year: 1997).*
Faure et al ("Molecular Embryology of the Foregut," JPGN vol. 52, Supplement 1, May 2011) (Year: 2011).*
Forster et al. "Human intestinal tissue with adult stem cell properties derived from pluripotent stem cells." Stem Cell Reports . Jun. 3, 2014;2(6):838-52. (Year: 2014).*
Iwao et al. "Generation of enterocyte-like cells with pharmacokinetic functions from human induced pluripotent stem cells using small-molecule compounds." Drug Metab Dispos. Apr. 2015;43(4):603-10. (Year: 2015).*
DiMarco et al. "Engineering of Three-Dimensional Microenvironments to Promote Contractile Behavior in Primary Intestinal Organoids." Integr Biol (Camb). Feb. 2014; 6(2): 127-142. (Year: 2014).*
Tyagi et al. "Pouch colon associated with anorectal malformations fails to show spontaneous contractions but responds to acetylcholine and histamine in vitro."J Pediatr Surg.Nov. 2009;44(11):2156-62. (Year: 2009).*

(Continued)

*Primary Examiner* — Titilayo Moloye
(74) *Attorney, Agent, or Firm* — Oliff PLC

(57) ABSTRACT

A gut organoid includes a tissue structure that encloses a cavity. A method of using the gut organoid includes providing a test drug to the gut organoid in the presence of a buffer solution so that liquid comprising the test drug enters into the cavity, and collecting and analyzing the liquid in the cavity. A method for producing the gut organoid includes plating cells on a cell culture substrate including a surface on which a cell-adhesive region and a non-cell-adhesive region surrounding the cell-adhesive region are formed, and culturing the cells plated on the cell culture substrate so as to induce differentiation of the cells.

32 Claims, 32 Drawing Sheets
Specification includes a Sequence Listing.

(56) References Cited

OTHER PUBLICATIONS

Finkbeiner et al. "Stem cell-derived human intestinal organoids as an infection model for rotaviruses." mBio. Jul. 3, 2012;3(4):e00159-12. (Year: 2012).*

Spence et al. "Directed differentiation of human pluripotent stem cells into intestinal tissue in vitro." Nature. Feb. 3, 2011; 470(7332): 105-109. (Year: 2011).*

Coletta et al. "Exogenous transforming growth factor-ß1 enhances smooth muscle differentiation in embryonic mouse jejunal explants." J Tissue Eng Regen Med. Jan. 2018; 12(1): 252-264. Published online Apr. 27, 2017. doi: 10.1002/term.2409 (Year: 2017).*

Spence, Jason et al., "Directed differentiation of human pluripotent stem cells into intestinal tissue in vitro." Nature. vol. 470 (7332); 2011; pp. 105-109 with Supplementary Information.

Makino, Hatsune et al., "Mesenchymal to embryonic incomplete transition of human cells by chimeric OCT4/3 (POU5F1) with physiological co-actovator EWS." Elsevier. Experimental Cell Research. vol. 315(16). 2009. pp. 2727-2740.

Toyoda, Masashi et al. "Lectin microarray analysis of pluripotent and multipotent stem cells." Genes to Cells. vol. 16(1). 2011. pp. 1-11.

Nishino, Koichiro et al. "Defining Hypo-Methylated Regions of Stem Cell-Specific Promoters in Human iPS Cells Derived from Extra-Embryonic Amnions and Lung Fibroblasts." PLoS ONE. 2010. vol. 5, Issue 9. pp. 1-9.

Okochi, Norihiko et al. "Encouraging Effect of Cadherin-Mediated Cell-Cell Junctions on Transfer Printing of Micropatterned Vascular Endothelial Cells." Langmuir. vol. 25(12). 2009. pp. 6947-6953.

Sasai, Yoshiki "Cytosystems dynamics in self-organization of tissue architecture." Nature. vol. 493. 2013. pp. 318-326.

Akatsu, Hidenori et al. "Xenogenic-free defined conditions for derivation and expansion of human embryonic stem cells with mesenchymal stem cells." JSRM. Regenerative Therapy. vol. 1. 2015. pp. 18-29.

Gracz, A. D. et al. "Defining hierarchies of stemness in the intestine: evidence from biomarkers and regulatory pathways." American Physiological Society. Am J Physiol Gastroinest Liver Physiol. vol. 307(3). 2014. pp. G260-G273.

Mittal, Ravinder K. et al. "Synchrony between circular and longitudinal muscle contractions during peristalsis in normal subjects." American Physiological Society. Am J Physiol Gastroinest Liver Physiol. vol. 290(3). 2006. pp. G431-G438.

Huizinga, Jan D. et al. "Gut peristalsis is governed by a multitude of cooperating mechanisms." American Physiological Society. Am J Physiol Gastroinest Liver Physiol. vol. 296(1). 2009. pp. G1-G8.

Sanders, Kenton M. et al. "Interstitial Cells of Cajal as Pacemakers in the Gastrointestinal Tract." Department of Physiology and Cell Biology, University of Nevada. Annu Rev Physiol. vol. 68. 2006. pp. 307-343.

McGrath, Kathleen et al. "Embryonic Expression and Function of the Chemokine SDF-1 and Its Receptor, CXCR4." Department of Pediatrics and Cancer Center, University of Rochester Medical Center. Developmental Biology. vol. 213(2). 1999. pp. 442-456.

Mawe, Gary M. et al. "Serotonin Signaling in the Gastrointestinal Tract." National Institutes of Health. Nat Rev Gastroenterol Hepatol. vol. 10(8). 2013. pp. 473-486.

Lahar, Nicholas et al. "Intestinal Subepithelial Myofibroblasts Support in vitro and in vivo Growth of Human Small Intestinal Epithelium." PLoS ONE. 2011. vol. 6, Issue 11. pp. 1-9.

Groneberg, David A. et al. "Intestinal peptide transport: ex vivo uptake studies and localization of peptide carrier PEPT1." American Physiological Society. Am J Physiol Gastrointest Liver Physiol. vol. 281(3). 2001. pp. G697-G704.

Dekkers, Johanna F. et al. "A functional CFTR assay using primary cystic fibrosis intestinal organoids." Nature Medicine. vol. 19, No. 7. 2013. pp. 939-945.

Watson, Carey L. et al. "An in vivo model of human small intestine using pluripotent stem cells." Department of Health and Human Services. Nature Medicine. vol. 20(11). 2014. pp. 1310-1314.

Uchida, Hajime et al. "A xenogeneic-free system generating functional human gut organoids from pluripotent stem cells." JCI Insight. 2017. pp. 1-13.

Workman, Michael J. et al. "Engineered human pluripotent-stem-cell-derived intestinal tissues with a functional enteric nervous system." Nature Medicine. vol. 23, Issue 1. 2017. pp. 49-59 with Supplementary Figures and Videos.

Akutsu, Hidenori. "Production of human miniature guts: Developement of new biological models for small bowel research." The 28th Annual Meeting of Japanese Society for Small Bowel Transplantation. Mar. 12, 2016.

Ueda, Takeshi et al. "Generation of functional gut-like organ from mouse induced pluripotent stem cells." Elsevier. Biochemical and Biophysical Research Communications. vol. 391. 2010. pp. 38-42.

Yamada, Takatsugu et al. "In Vitro Functional Gut-Like Organ Formation from Mouse Embryonic Stem Cells." Stem Cells. vol. 20. 2002. pp. 41-49.

Akatsu, Hidenori. "Production of human miniature guts—Development of new biological models for small bowel research." The 28th Annual Meeting of Japanese Society for Small Bowel Transplantation. Center for Regenerative Medicine, National Center for Child Health and Development. Mar. 12, 2016.

National Center for Child Health and Development. Press Release. Jan. 6, 2017.

National Center for Child Health and Development. Web Article. Jan. 12, 2017.

Uchida, Hajime et al. "A xenogeneic-free system generating functional human gut organoids from pluripotent stem cell" JCI Insight. vol. 2(1). 2017.

Hidenori, Akutsu. "Creating a gut from ES cells aiming for treatment of children." Nikkei Science. 2017. pp. 9-11.

Uchida, Hajime. "A Xenogenic-Free System Generating Functional Mini-Guts from Human Embryonic Stem Cells." International Society for Stem Cell Research. 2017.

Jul. 3, 2018 Written Opinion issued in PCT/JP2018/013950.

* cited by examiner

GUT ORGANOID AND METHOD FOR PRODUCING THE SAME

This is a Continuation of Application No. PCT/JP2018/013950, filed Mar. 30, 2018, which claims priority to JP 2017-115952, filed Jun. 13, 2017. The disclosures of the prior applications are hereby incorporated by reference herein in their entireties.

BACKGROUND

Technical Field

The present disclosure relates to a gut organoid having gut-like functions and a method for producing the same.

Description of the Related Art

The intestine is a complex organ including cells derived from all 3 germ layers (endoderm, ectoderm, and mesoderm). The intestine, which is composed of endoderm-derived intestinal epithelial cells (e.g., intestine cells, goblet cells, endocrine cells, brush cells, Paneth cells, and M cells), mesoderm-derived lymph tissue, smooth muscle cells, interstitial cells of Cajal, ectoderm-derived intestinal nerve plexus, and other types of cells in a complex manner, has a variety of functions including secretion, absorption, and peristaltic movement.

Meanwhile, as pluripotent stem cells such as embryonic stem cells (ES cells) and induced pluripotent stem cells (iPS cells) can be induced to differentiate into cells of interest, clinical applications of pluripotent stem cells in the field of regenerative medicine are expected.

In recent years, the technology for producing a "gut organoid" having gut-like functions from pluripotent stem cells or isolated tissue progenitors was reported (e.g., Non Patent Literature 1).

Patent Literature 1 discloses a method for constructing gut tube-like cell mass having the intramural nervous system, comprising: step (a) of collecting undifferentiated embryonic stem cells, performing hanging drop culture of the collected undifferentiated embryonic stem cells in a medium containing BDNF so as to induce embryoids; and step (b) of allowing the embryoids induced in the step (a) to adhere to a culture dish and further performing culture.

Patent Literature 2 discloses a method for producing an artificial intestine tract, comprising culturing embryoids formed from purified iPS cells using a three-dimensional culture system, and then, culturing the embryoids using a two-dimensional adhesion culture system, thereby inducing differentiation into an intestine tract.

Patent Literature 3 discloses a method for inducing induced pluripotent stem cells to differentiate into intestinal epithelial cells, comprising the following steps (1) to (3): step (1) of allowing induced pluripotent stem cells to differentiate into endoderm-like cells; step (2) of allowing the endoderm-like cells obtained in the step (1) to differentiate into intestinal stem cell-like cells; step (3) of allowing the intestinal stem cell-like cells obtained in the step (2) to differentiate into intestinal epithelial cell-like cells, wherein culture is performed in the presence of EGF and at least one compound selected from the group consisting of an MEK1 inhibitor, a DNA methylation inhibitor, and a TGFβ receptor inhibitor.

Patent Literature 4 discloses a method for producing an intestinal structure from embryonic stem cells and/or induced pluripotent stem cells, comprising performing cell culture on a substrate on which a pattern of cell-adhesive regions each having a certain area is formed.

Patent Literature 5 discloses a method for inducing differentiation of induced pluripotent stem cells into endodermal cells, comprising performing cell culture on a substrate on which a pattern of cell-adhesive regions each having a certain area is formed.

Meanwhile, as a method for testing efficacy of a drug that acts on the intestine, a bidirectional transcellular transport capacity assay (Caco-2 transmembrane permeability assay) using cells overexpressing Caco-2 cells or a particular transporter is known.

CITATION LIST

Patent Literature

Patent Literature 1: JP Patent Publication (Kokai) No. 2006-239169 A
Patent Literature 2: WO2010/143747
Patent Literature 3: WO2014/132933
Patent Literature 4: JP Patent Publication (Kokai) No. 2014-236716 A
Patent Literature 5: JP Patent Publication (Kokai) No. 2015-15943 A

Non Patent Literature

Non Patent Literature 1: Spence J R, et al. Directed differentiation of human pluripotent stem cells into intestinal tissue in vitro. Nature. 2011; 470 (7332): 105-109

SUMMARY

Caco-2 is a colon adenocarcinoma cell and cannot be said to accurately reflect the absorption of low-molecular-weight compounds by small-intestinal epithelial cells. In Caco-2 cell membrane permeability assay, a single layer film is formed on a semi-permeable membrane (transwell) which must be free of leakage. The assay requires several preliminary steps including measurement of transepithelial electrical resistance (TEER) in advance, which makes the operation complicated. In addition, upon TEER measurement, a Caco-2 cell membrane is often damaged with an electrode, which is problematic.

When it becomes possible to produce a gut organoid having gut-like functions, it is expected to be useful for the development of drugs for preventing or treating intestinal diseases and pathological studies on intestinal diseases. However, conventionally available gut organoids are not always satisfactory.

The method disclosed in Non Patent Literature 1 is intended to treat human pluripotent stem cells with activin to perform culture by inducing differentiation into endoderm while preventing differentiation into mesoderm and ectoderm so as to prepare an intestinal epithelial structure, prepare neural crest cells, and combine both, thereby producing gut organoids. This method is complicated in the operation and does not mimic the natural occurrence of the three germ layers in the living body.

In addition, cell constructs produced by the methods disclosed in Patent Literature 1 to 5 do not have gut-like functions, indicating that there was still room for improvement.

In view of the above, the present disclosure provides a gut organoid having gut-like functions, a method for producing the same, a medium suitable for producing a gut organoid, and a kit suitable for producing a gut organoid. Specifically, the present disclosure encompasses the following embodiments.

A gut organoid including a tissue structure that encloses a cavity, wherein: the tissue structure comprises endodermal cells, mesodermal cells, and ectodermal cells; and the endodermal cells comprise intestinal epithelial cells that are at least part of an outer surface of the tissue structure.

A gut organoid including a tissue structure that encloses a cavity, wherein: an outer surface of the tissue structure comprises an intestinal epithelium; and the tissue structure further comprises at least one of intestinal nerve cells, smooth muscle cells, or interstitial cells of Cajal.

A gut organoid including a tissue structure that encloses a cavity, wherein: an outer surface of the tissue structure comprises at least one of enterocytes, goblet cells, enteroendocrine cells, or Paneth cells; and the tissue structure further comprises at least one of intestinal nerve cells, smooth muscle cells, or interstitial cells of Cajal.

The present description includes part or all of the contents as disclosed in the description and/or drawings of Japanese Patent Application No. 2017-115952, which is a priority document of the present application.

Figure 1A:
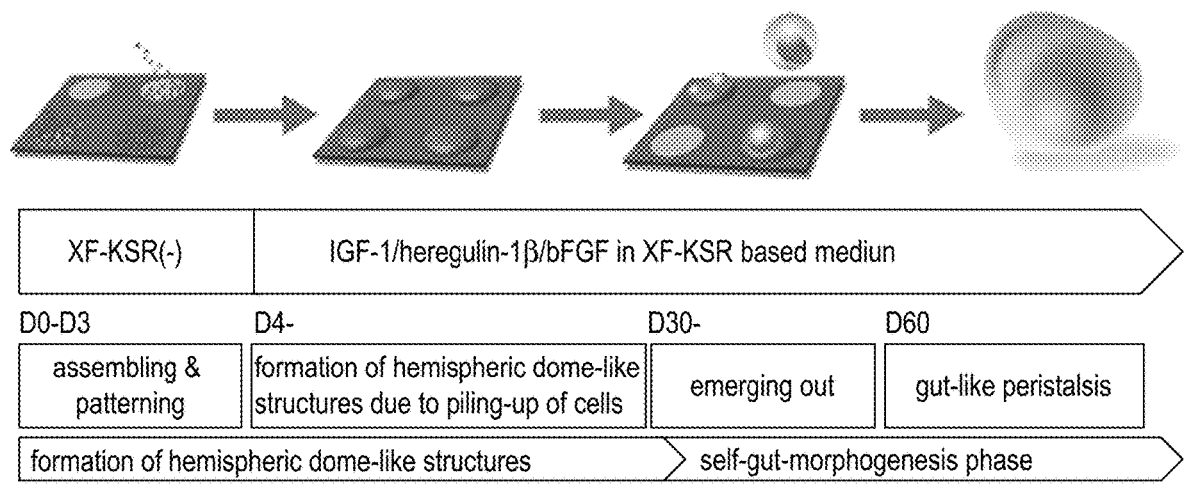
FIG. 1A schematically illustrates the process of gut organoid generation from human pluripotent stem cells on a cell culture substrate on which cell-adhesive regions are patterned.
Figure 1B:
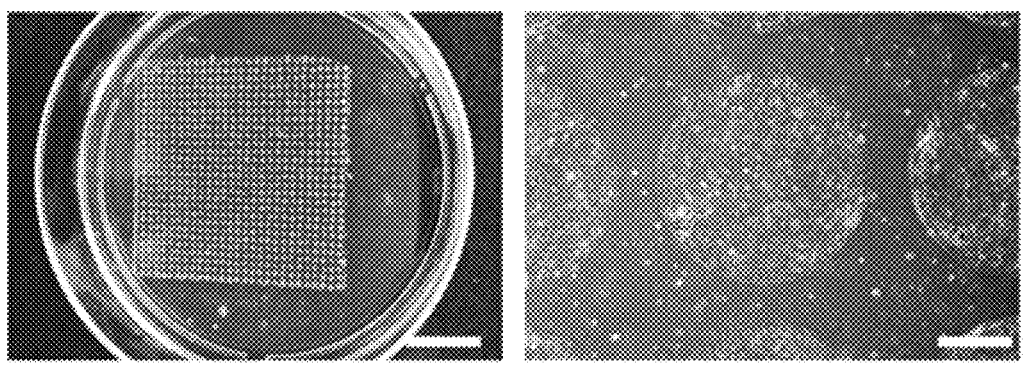

The left panel in FIG. 1B shows many patterned hydrophilic polymer-coated circular cell-adhesive regions 1.5 mm in diameter formed on a cell culture substrate (scale bar:15 mm). The right panel in FIG. 1B shows that human ES cells attached and grew only within each circular cell-adhesive region (scale bar: 500 μm).

Figure 1C:
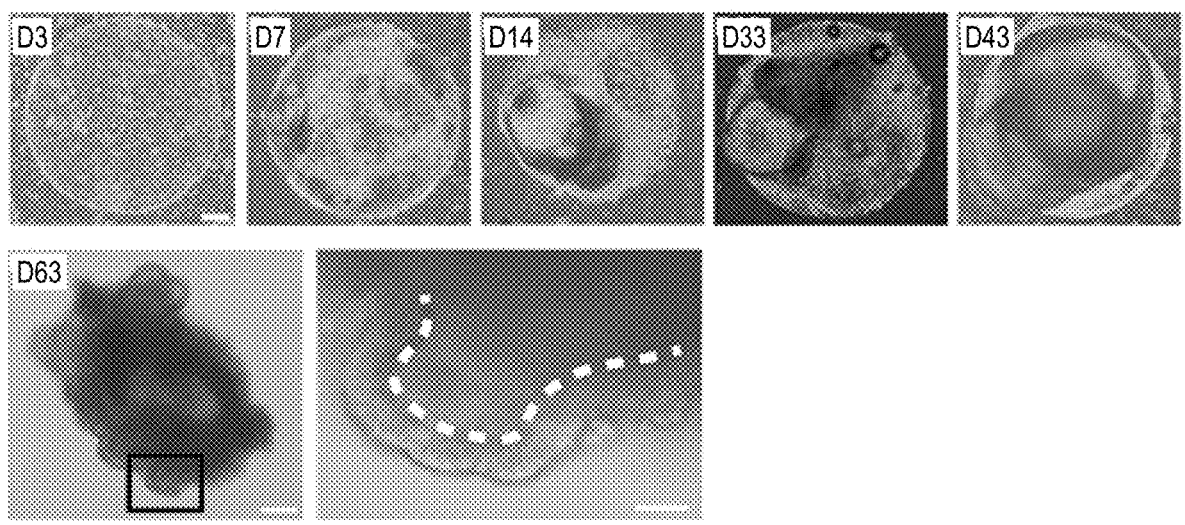

FIG. 1C shows images indicating the time course of organoid growth in culture. In FIG. 1C, D3, D7, D14, D33, D43, and D63 represent days 3, 7, 14, 33, 43, and 63 in culture, respectively. In FIG. 1C, the scale bar for the upper panels and the lower right panel represents 200 and the scale bar for the lower left panel represents 50 μm.

Figure 1D:
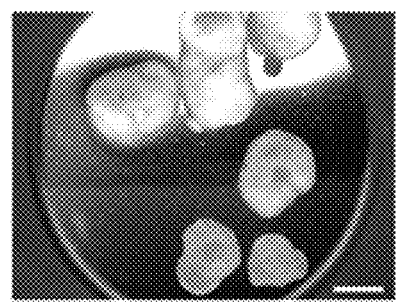

FIG. 1D shows an image of six organoids that were maintained to have gut-like motor activity on day 129 in culture. In FIG. 1D, the scale bar represents 5 mm.

Figure 2A:
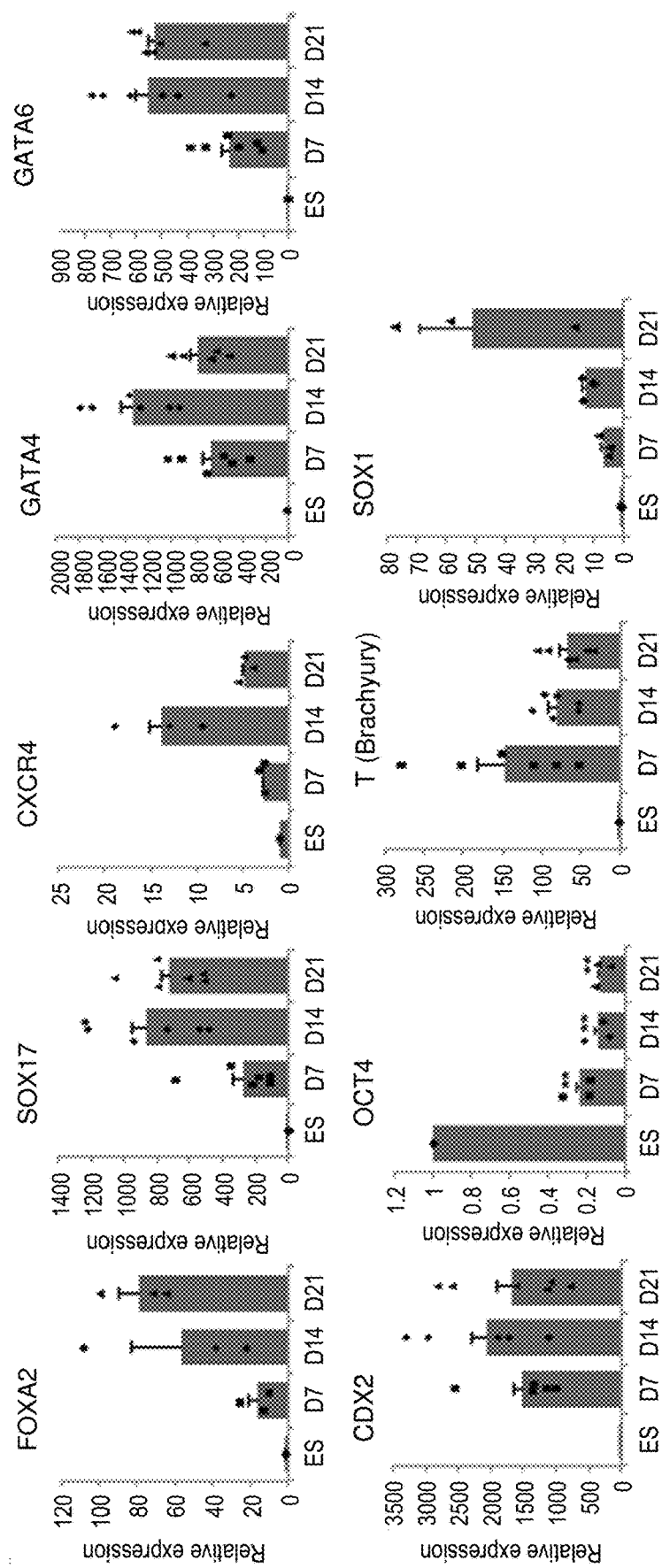

FIG. 2A shows the results of analysis of expression levels of biomarker genes at different time points in culture of human embryonic stem cells (hESCs). The data are reported as mean±SEM. Statistically significant differences were identified between embryonic stem (ES) vs. day 7, ES vs. day 14, and ES vs. day 21 using Student's t test (P<0.01) (n=3-6). Expression levels reported as means±SEM of relative expression levels to GAPDH. ES, D7, D14, and D21 on the horizontal axis represent undifferentiated ES cells, day 7 organoids, day 14 organoids, and day 21 organoids, respectively. Statistically significant differences between expression levels in organoids at different time points and expression levels in undifferentiated ES cells were examined by the Student's t test (P<0.01) (n=3-6).

Figure 2B:
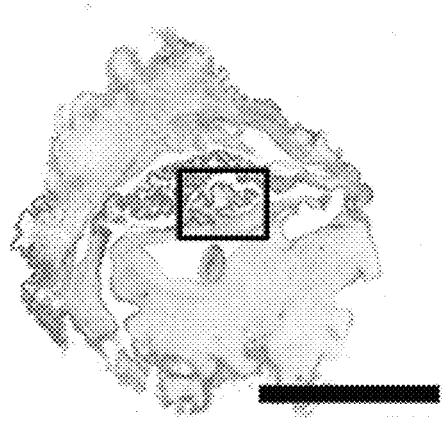
Figure 2B:
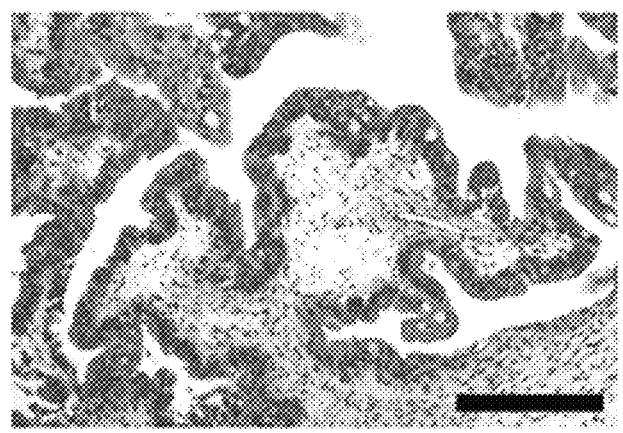

FIG. 2B shows the results of H&E staining of motile gut organoids on day 100 in culture. In FIG. 2B, the scale bar in the left panel represents 2 mm, and the scale bar in the right panel represents 200 μm.

Figure 2C:
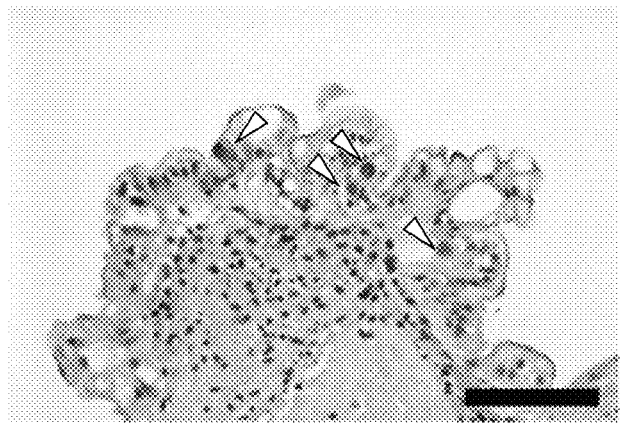

FIG. 2C shows the results of Alcian Blue staining of differentiated organoids on day 60 in culture. In FIG. 2C, the scale bar represents 100 μm. Arrowheads indicate sites where goblet cells were observed.

Figure 2D:
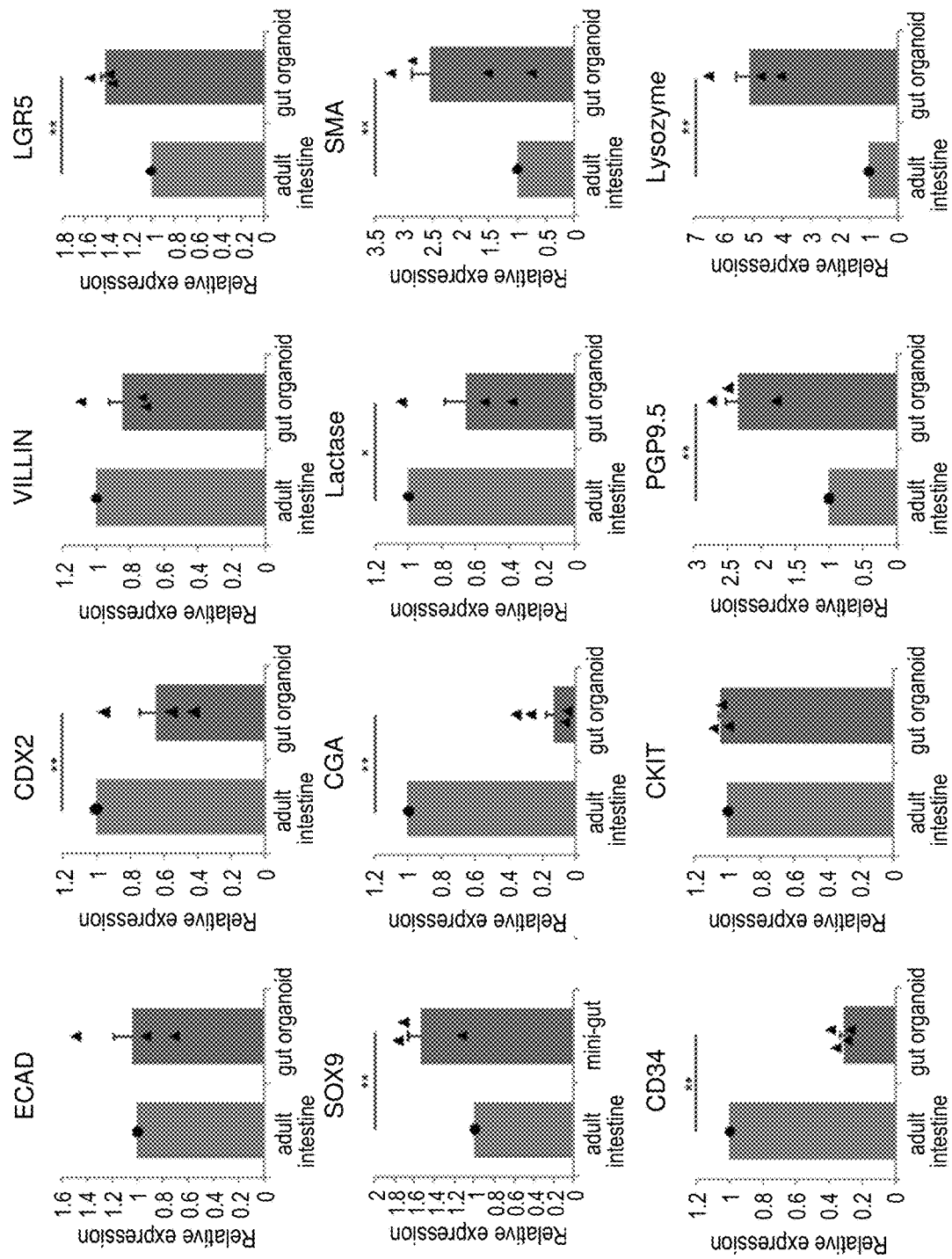

FIG. 2D shows the relative expression levels of cell marker genes in day 50 differentiated gut organoids and the human adult small intestine. Statistically significant differences between expression levels in the organoids and expression levels in the human adult small intestine were examined by the Mann-Whitney rank-sum test (*P<0.05, **P<0.01). In FIG. 2D, expression levels are reported as means obtained from three independent experiments (m=3-4)±SEM.

Figure 3A:
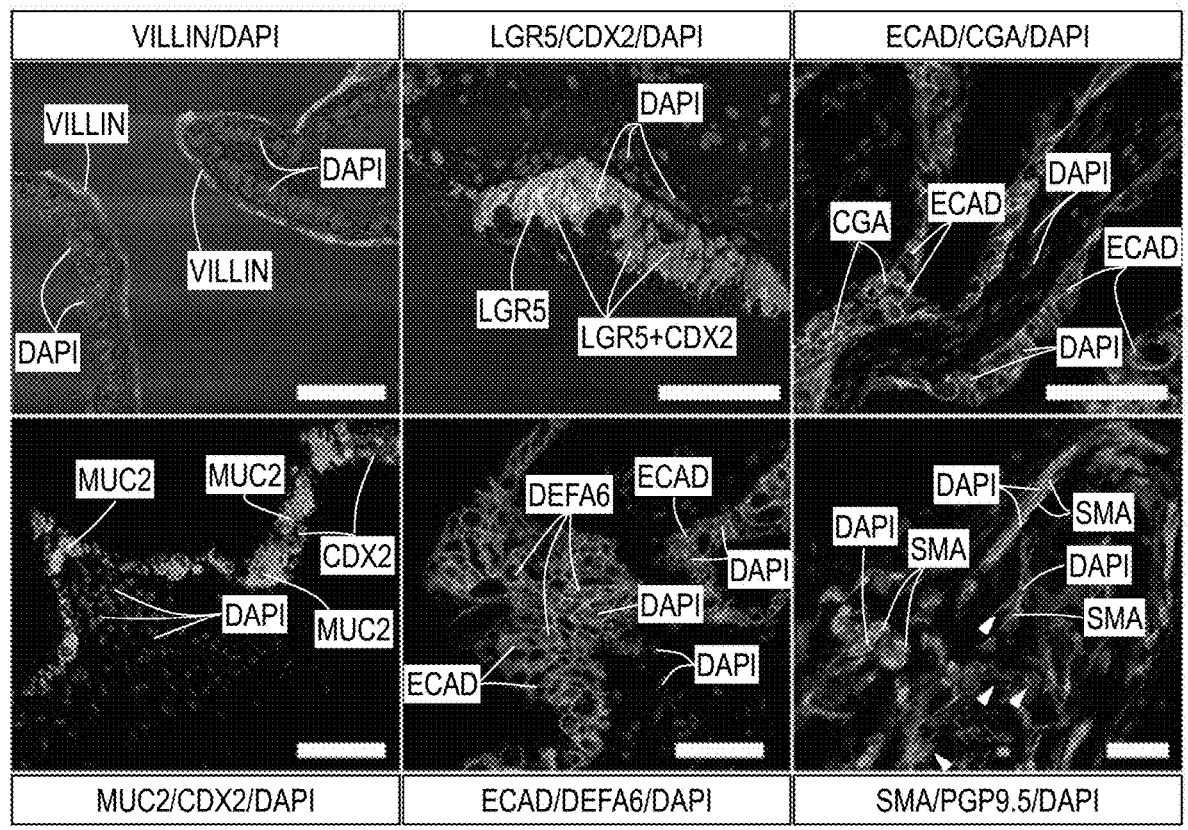

FIG. 3A shows the results of immunostaining of day 50-60 organoids obtained from human embryonic stem cells (hESC) with intestinal differentiation markers. Villin, leucine-rich repeat containing G protein-coupled receptor 5 (LGR5), CDX2, E-cadherin (ECAD), chromogranin A (CGA), mucin-2 (MUC2), Paneth cell-specific defensin α-6 (DEFA6), α-smooth muscle actin (SMA), and protein gene product 9.5 (PGP9.5) were used as intestinal differentiation markers. Cell nuclei were counterstained with DAPI. In FIG. 3A, arrowheads in the lower right panel indicate PGP9.5-positive enteric neuronal cells in the α-SMA-positive smooth muscle layer. In FIG. 3A, the scale bars in the upper left, upper middle, and lower right panels each represent 50 μm, and the scale bars in the upper right panel, lower left panel, and lower middle panel each represent 100 μm.

Figure 3B:
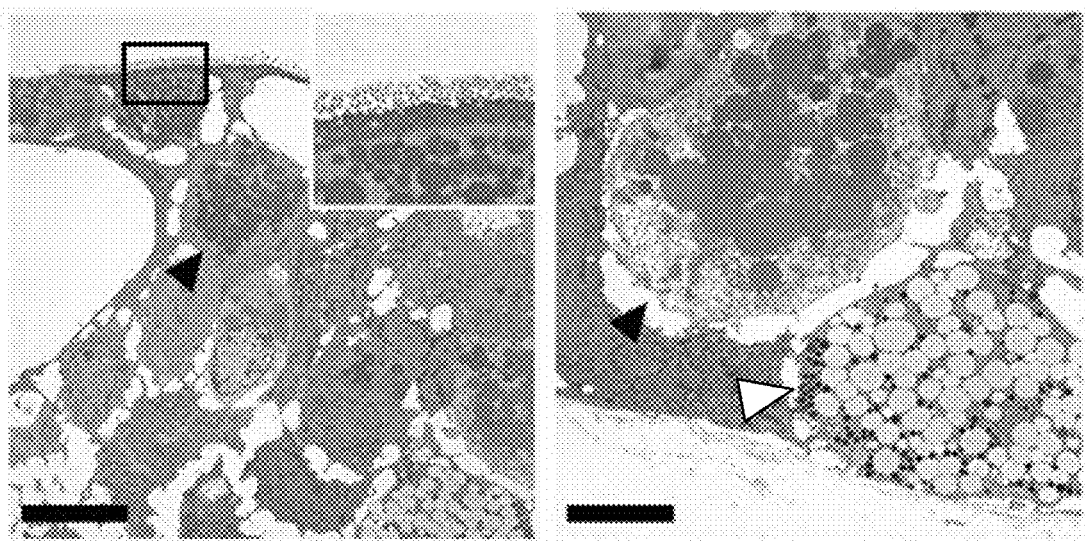

FIG. 3B shows electron microscopic observation images of enterocytes with brush border microvilli characteristic to the intestine (left panel), Paneth cells with secretory granules (black arrowhead), and goblet cells containing mucin granules (white arrowhead). In FIG. 3B, the scale bar in the left panel represents 10 μm, and the scale bar in the right panel represents 5 μm.

Figure 3C:
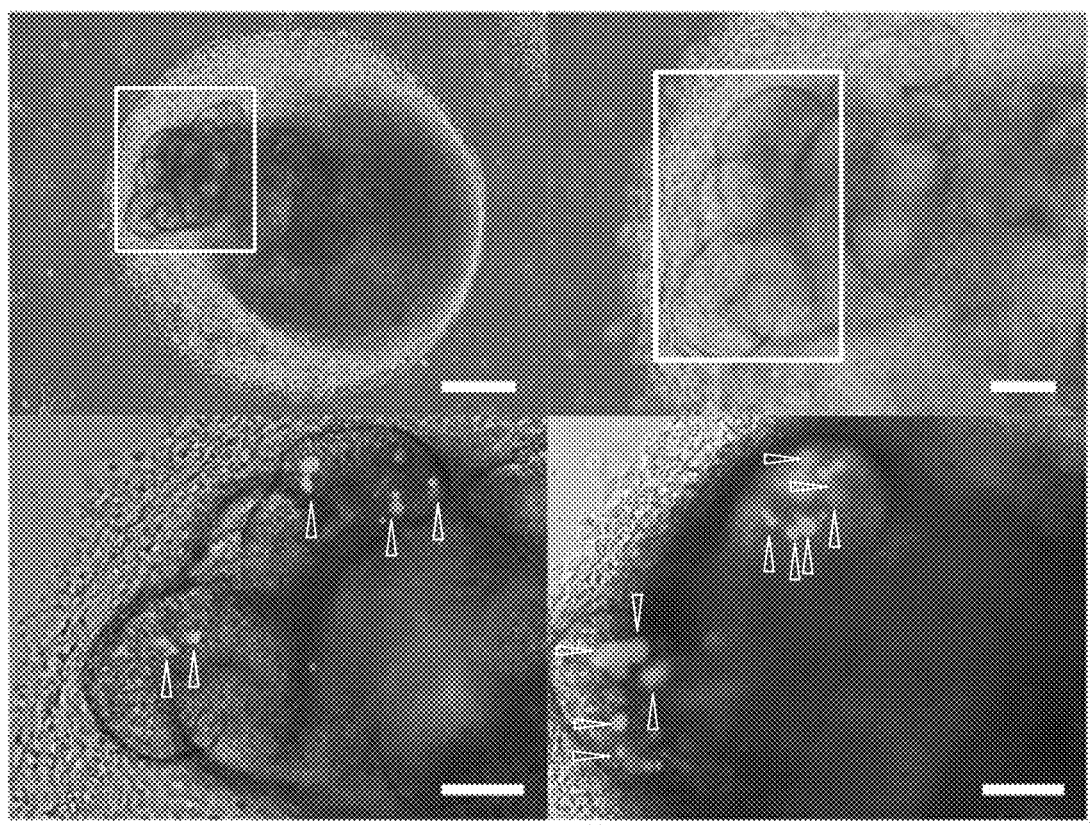

FIG. 3C indicates that organoids, which developed from human embryonic stem cells (hESCs) transfected with pPB-hLgr5p-EGFP-neo, expressed EGFP under LGR5 promoter regulation. Cells expressing EGFP in this experimental system are LGR5-positive cells. In FIG. 3C, the upper left panel shows a whole view of organoids on day 34 in culture, and the upper right panel shows a high-magnification view of a gut tube-like structure in the square box of the upper left panel. In FIG. 3C, the lower left panel shows a fluorescent microscopic observation image of the boxed area in the upper right panel. The observation image in the lower left panel in FIG. 3C shows that a relatively small number of EGFP-positive cells (arrowhead) were present in the gut organoid on day 34 in culture. The number of EGFP-positive cells (arrowhead) increased in the gut organoid on day 41 in culture (the lower right panel in FIG. 3C). In FIG. 3C, the scale bar in the upper left panel represents 300 μm, the scale bars in the upper right panel, lower left panel, and lower right panel each represent 100 μm.

Figure 4A:
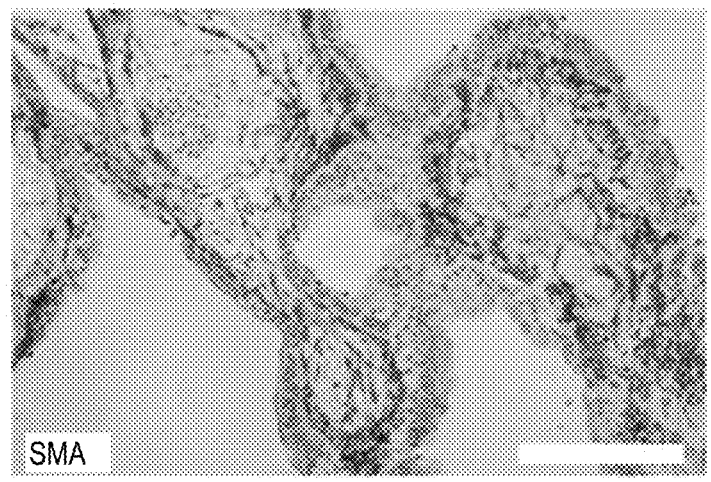

FIG. 4A shows an observation image of immunohistochemical staining for α-smooth muscle actin (SMA) in a day 60 gut organoid. The scale bar represents 200 μm.

Figure 4B:
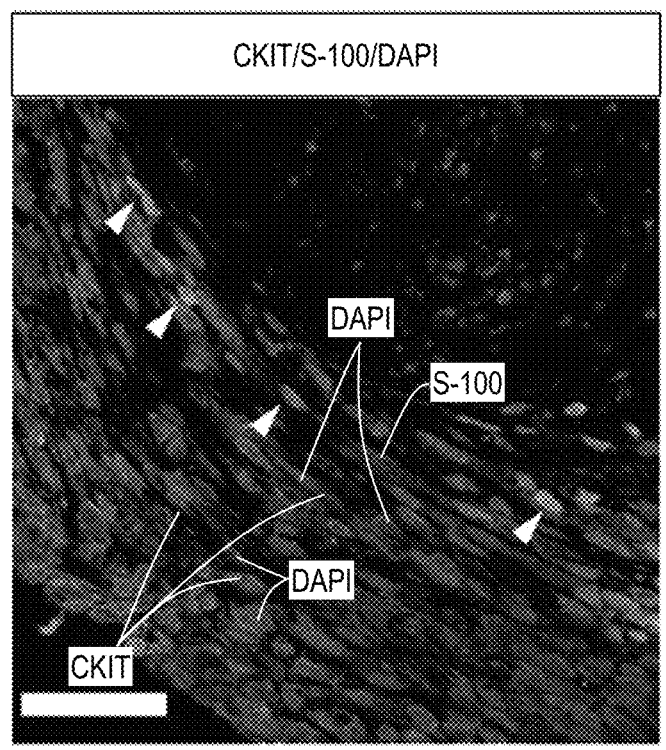

FIG. 4B shows the results of immunostaining of Cajal cells. The scale bar represents 50 μm. Arrowheads indicate CKIT and S-100 double-positive cells. CKIT and S-100 double-positive cells were observed within the myenteric and submucosal plexuses.

Figure 4C:
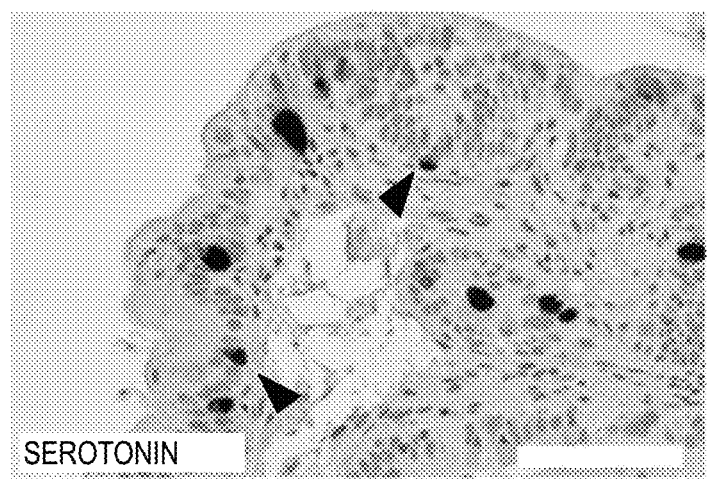

FIG. 4C shows the distribution of the neurotransmitter serotonin, an enteroendocrine cell marker in the day 60 gut organoid of human embryonic stem cells (hESCs). The scale bar represents 100 μm. Serotonin-positive cells indicated by arrowheads in FIG. 4C were observed in the lining epithelium and displayed a triangular shape.

Figure 4D:
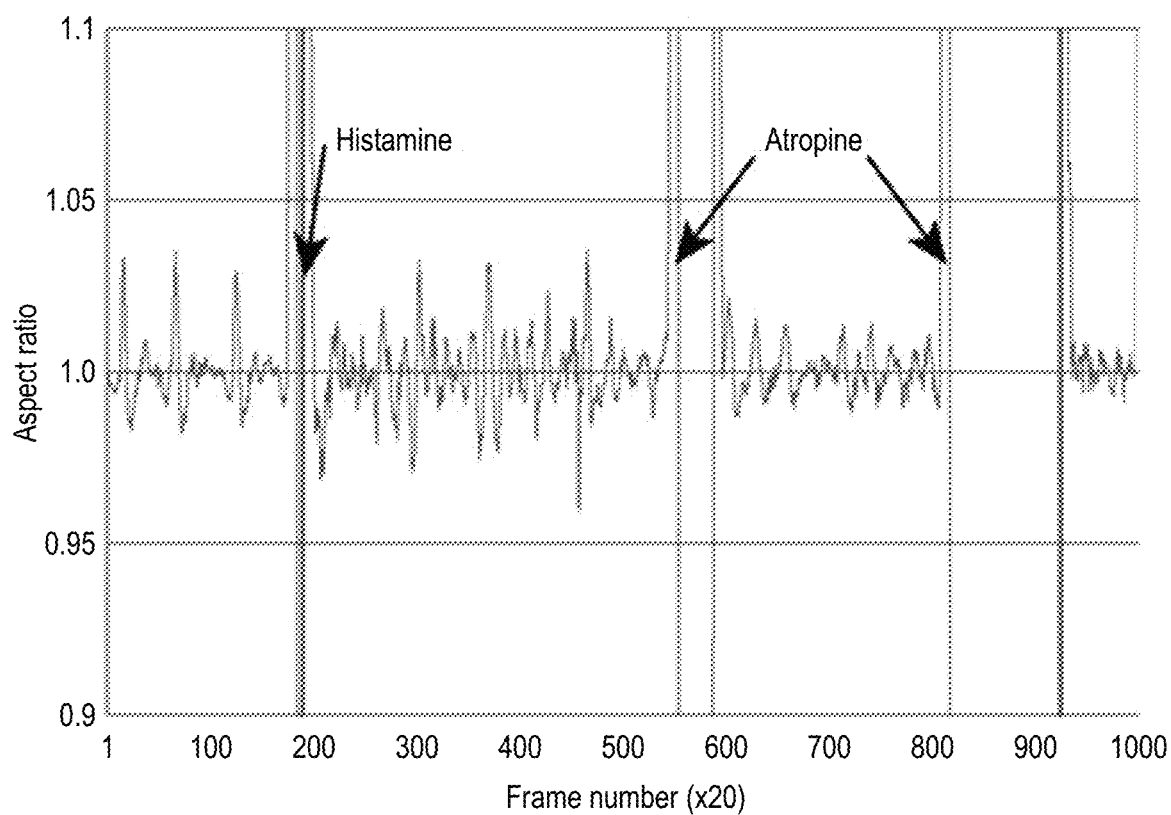

FIG. 4D shows contractile movement of the motile gut organoid. The vertical aspect ratios are based on the ratio of the longest diameter to the shortest diameter of the gut organoid, which were calculated for each frame. The video was recorded at 30 frames per second. FIG. 4D shows that waves of constant contractions started to be recorded before treatment (frames 1-160), histamine treatment increased the frequency of contractile movement in frequency, and atropine treatment decreased contraction amplitude and frequency.

Figure 4E:
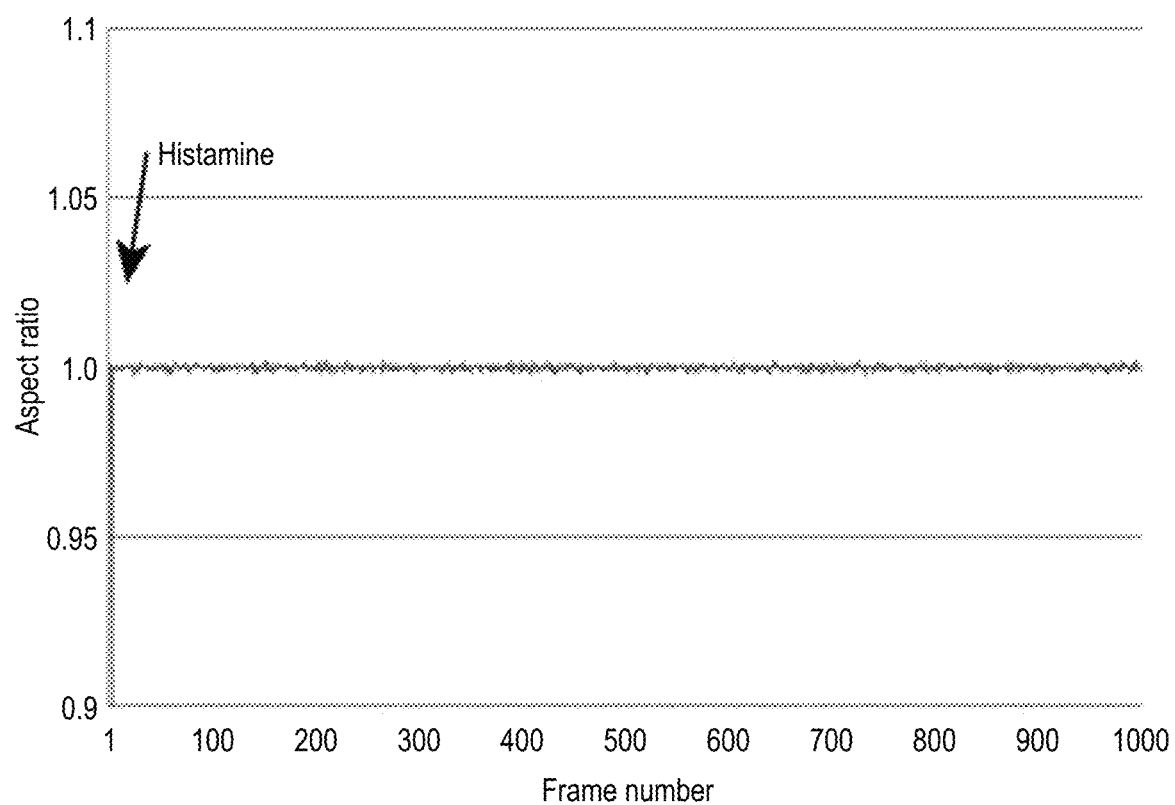

FIG. 4E indicates that nonmotile gut organoids did not show contractions in response to histamine treatment.

Figure 4F:
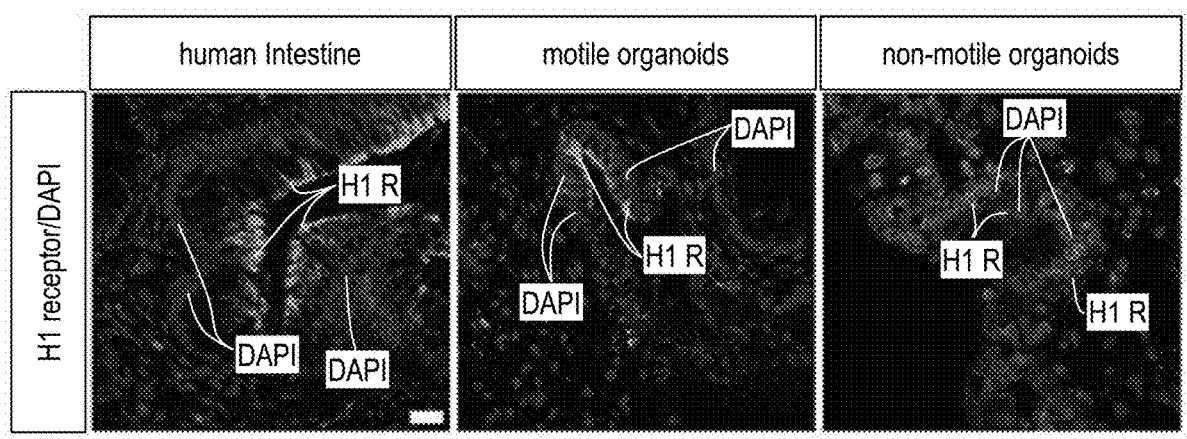

FIG. 4F shows the results of immunostaining for the histamine H1 receptor in human intestine tissue, motile gut organoids, and nonmotile gut organoids. Cell nuclei were counterstained with DAPI. Histamine H1 receptor-positive cells were observed in the epithelial and mesenchymal areas not only in motile gut organoids but also in nonmotile gut organoids In FIG. 4F, the scale bar represents 20 μm.

Figure 5A:
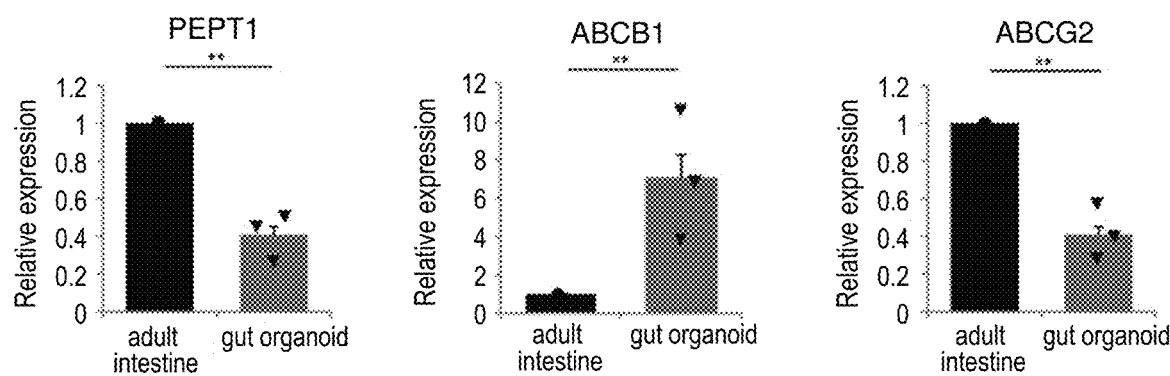

FIG. 5A shows the results of analysis of expression levels of the intestinal oligopeptide transporter (PEPT1) and major ATP-binding cassette (ABC) transporters ABCB1 and ABCG2 in day 50 hESC-derived gut organoids by quantitative RT-PCR and comparison to that in the healthy adult small intestine. Statistical analysis was performed using the t test or Mann-Whitney rank-sum test (**P<0.01). Data are shown as means (%)±SEM (n=3).

Figure 5B:
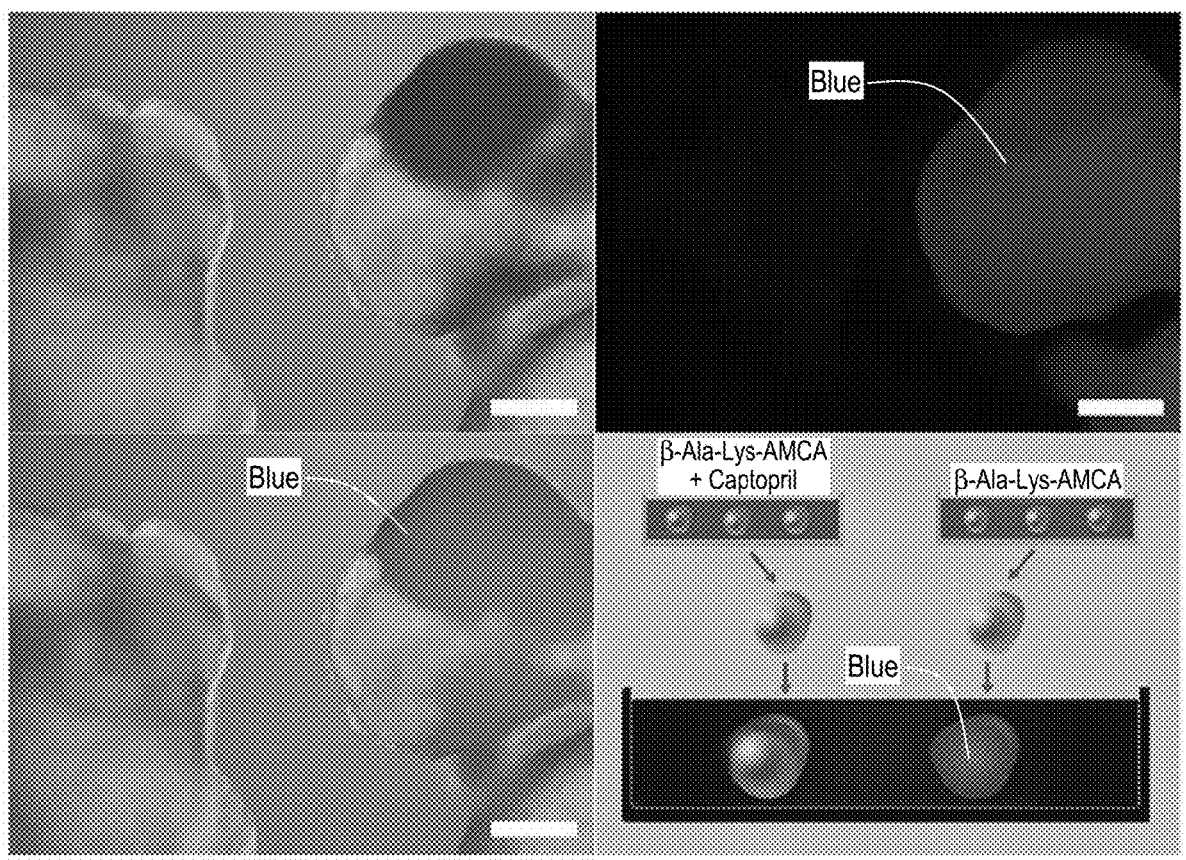

FIG. 5B shows the results of an experiment performed by treating gut organoids with fluorophore-conjugated β-Ala-Lys-AMCA with or without angiotensin-converting enzyme inhibitor captopril in the upper left and right panels and lower left panel. In each of the upper left and right panels and lower left panel in FIG. 5B, the left gut organoid was treated with the dipeptide with captopril, and the right gut organoid was treated with the dipeptide without captopril. In FIG. 5B, the upper left panel is a bright-field observation image, the upper right panel is a fluorescence observation image, and the lower left panel is a combined bright-field and fluorescence image. The sample size was set to n=3 for each group. The scale bar represents 200 μm. It was confirmed that gut organoids are capable of uptake of dipeptide and the uptake is inhibited by captopril. The lower right panel in FIG. 5B schematically shows the process of dipeptide uptake assay.

Figure 5C:
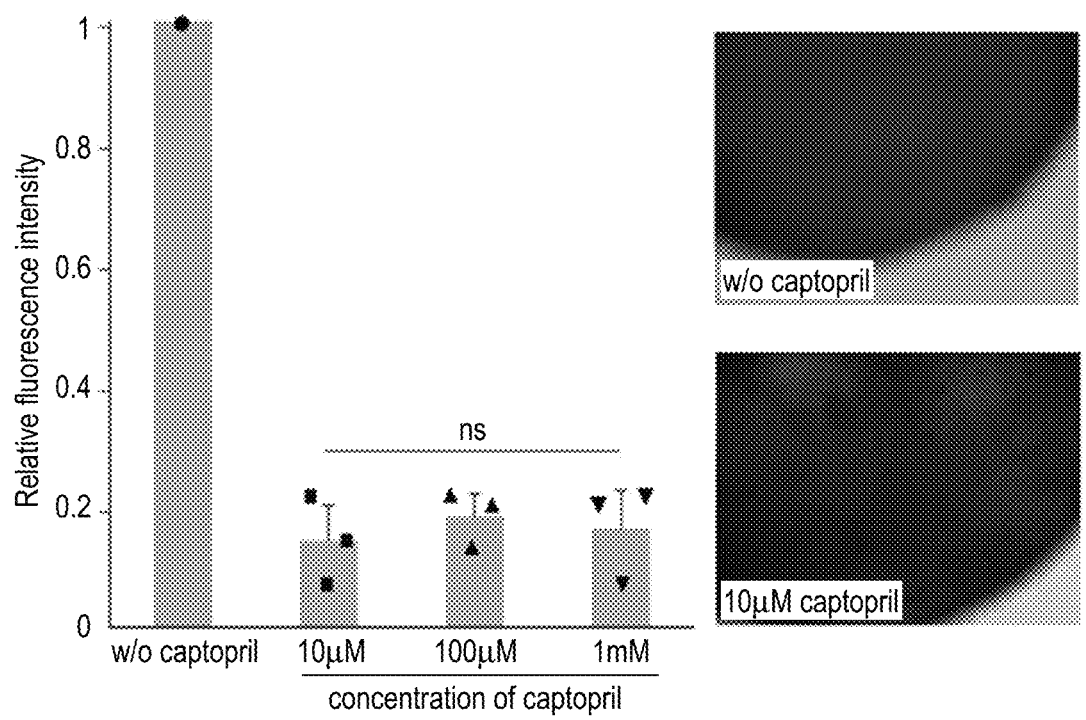

FIG. 5C shows the results of quantification. To quantify the uptake of β-Ala-Lys-AMCA, gut organoids were cultured with or without 10 μM, 100 μM, and 1 mM of captopril. The AMCA-related fluorescence signals were observed using a fluorescence microscope (BZ-X710; Keyence) equipped a top-stage incubator (5% $CO_2$ at 37° C.), and the fluorescence signal intensity was quantified by using Hybrid Cell Count BZ-H3C (Keyence). These results did not confirm captopril dose dependency.

Figure 6A:
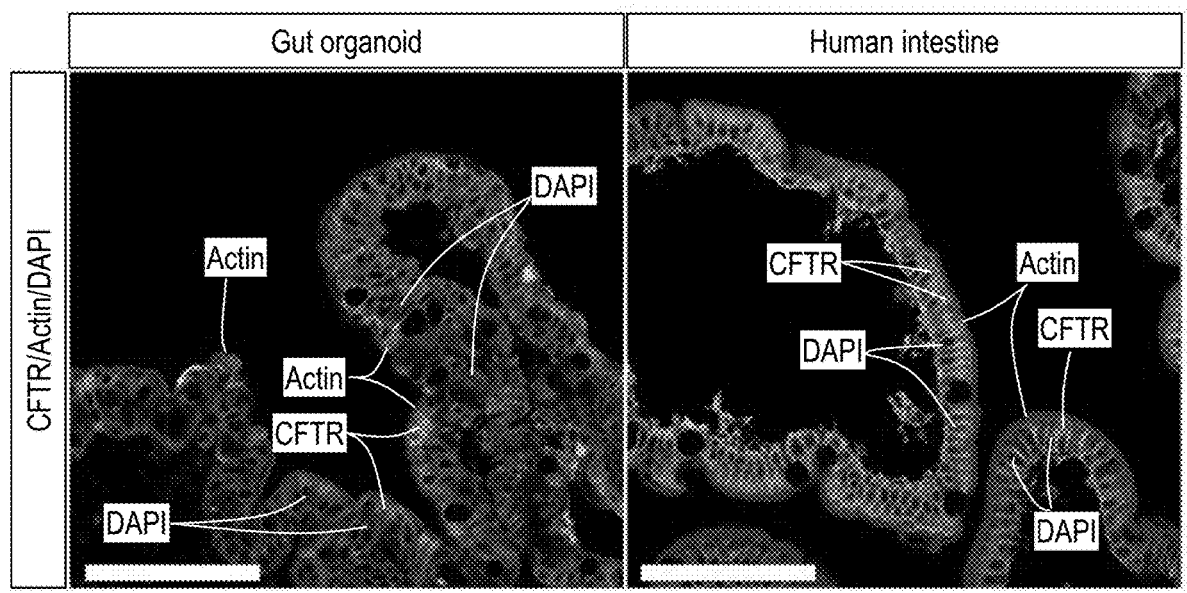

FIG. 6A shows observation images of fluorescent microscopic observation of day 115 gut organoids from human embryonic stem cells (hESC) immunostained with markers for the cystic fibrosis conductance regulator (CFTR). FIG. 6A shows the observation results for the gut organoid in the left panel and the human intestine in the right panel. CFTR, actin, and DAPI are shown.

Figure 6B:
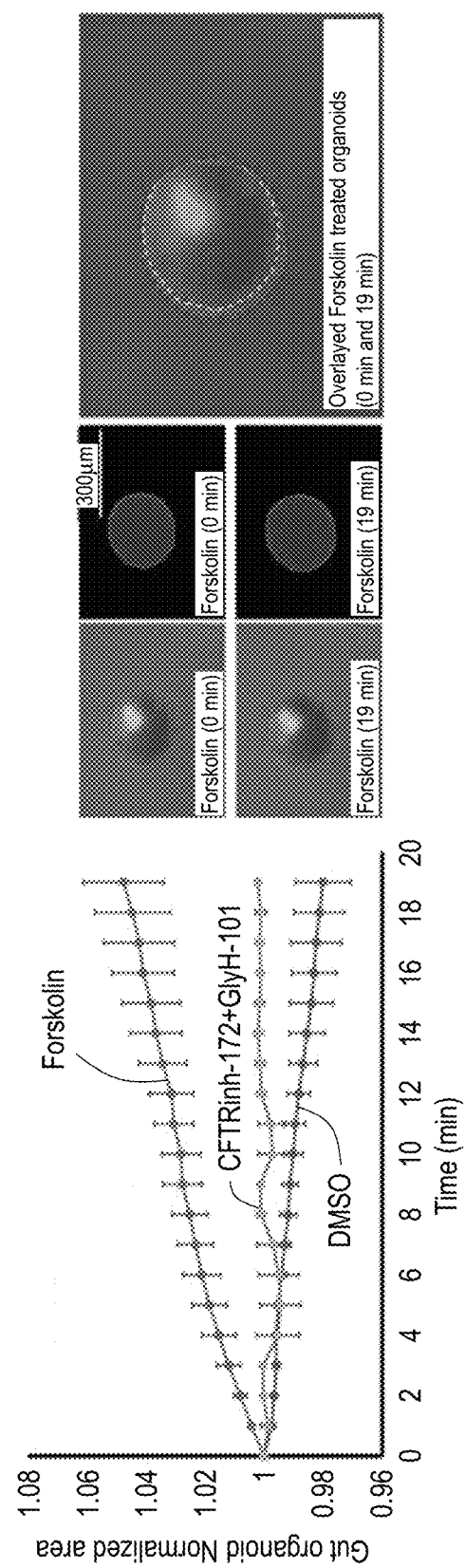

FIG. 6B indicates that forskolin induces gut organoid swelling. Gut organoids from human embryonic stem cells (hESCs) were monitored by time-lapse fluorescence laser confocal microscopy (Keyence). The gut organoid surface area was quantified using Hybrid Cell Count/BZ-H3C (Keyence). The normalized total organoid surface area was calculated and averaged from 3 individual wells per treatment under experimental conditions. The forskolin-induced organoid (19 minutes) was overlaid with a pretreated organoid (0 minutes; 569 μm).

Figure 7A:
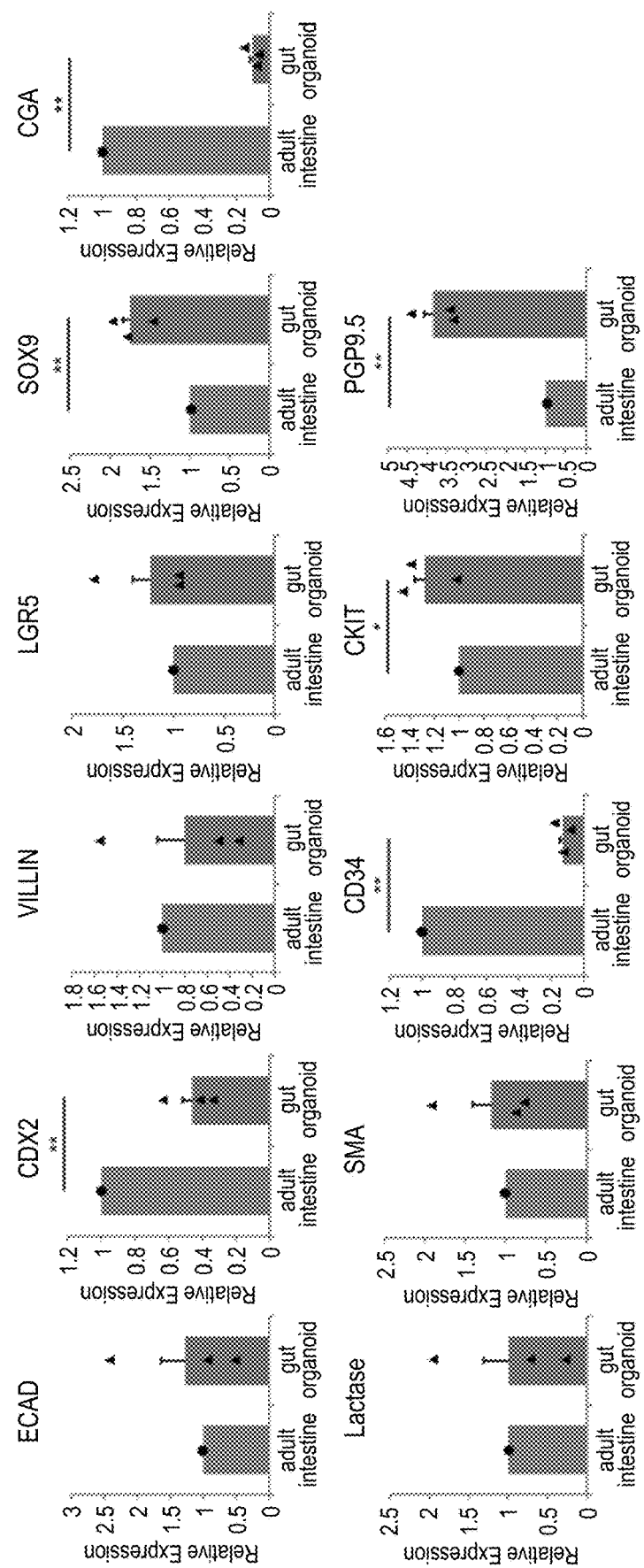

FIG. 7A shows the analysis results of expression levels of cells biomarkers in nonmotile differentiated gut organoids (on day 52 in culture). The expression levels of the markers are expressed as values normalized against the GAPDH expression level. The biomarker gene expression levels in nonmotile gut organoids were comparable to the gene expression levels in the adult small intestine. Statistical analysis was performed using the t test or Mann-Whitney rank-sum test (*<0.05, **P<0.01). Data are reported as means (%) SEM (n=3).

Figure 7B:
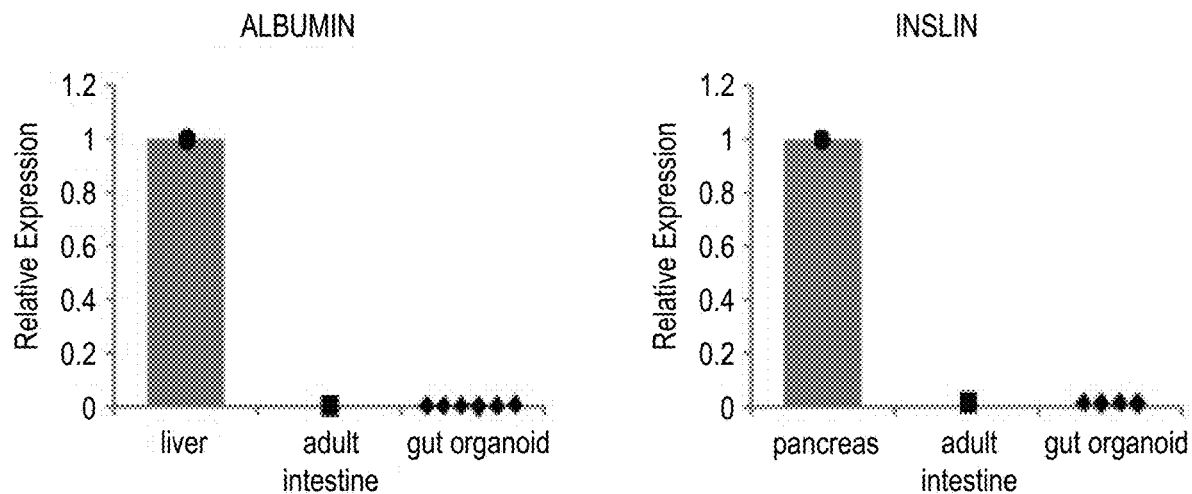

FIG. 7B shows the expression level of albumin or insulin in nonmotile gut organoids. Expression of these genes in gut organoids were not detectable. Data were obtained from 3 independent experiments (n=3-6).

Figure 7C:
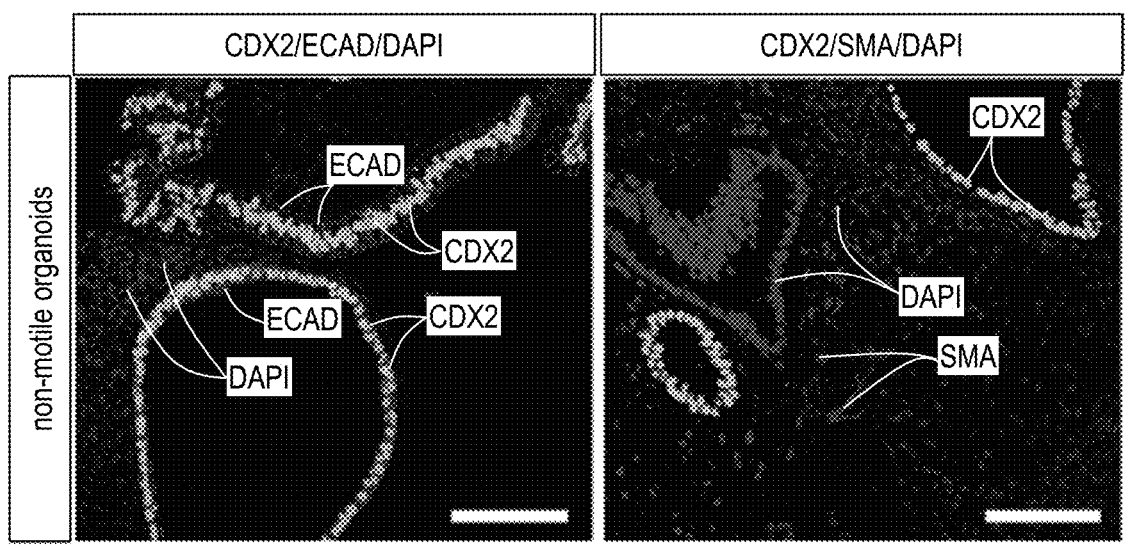

FIG. 7C shows the results of immunostaining with markers for CDX2, E-cadherin (ECAD), and α-smooth muscle actin (SMA) in nonmotile gut organoids. Cell nuclei were counterstained with DAPI. The scale bar represents 100 μm. Non-motile organoids showed CDX2 and ECAD-positive epithelial layers, but a very low expression level of SMA in the mesenchymal area.

Figure 7D:
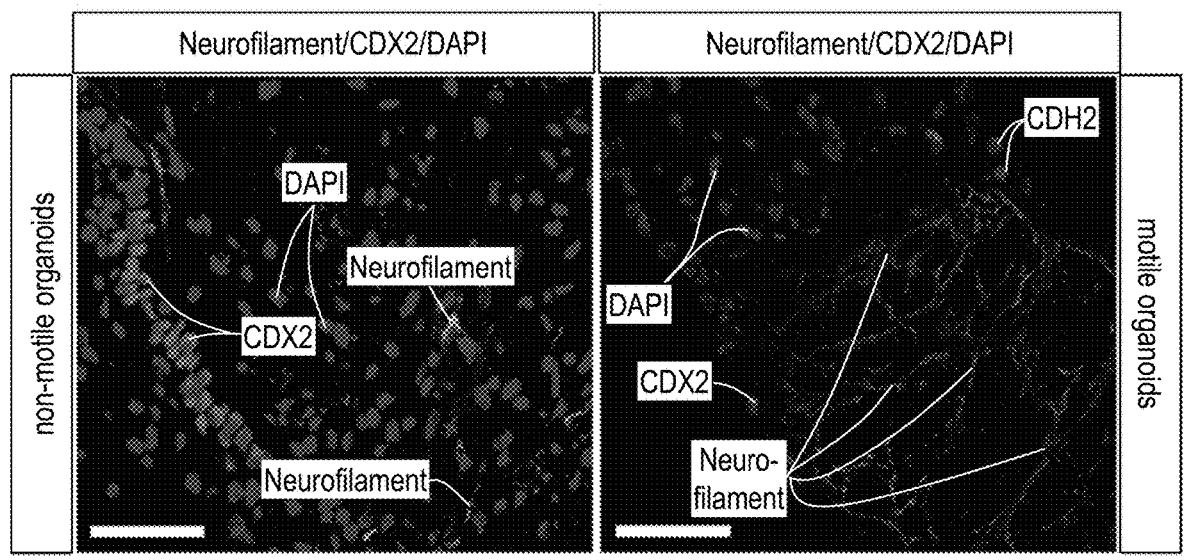

The left panel in FIG. 7D shows the results of immunostaining of nonmotile gut organoids for neurofilaments and CDX2. Cell nuclei were counterstained with DAPI. The right panel in FIG. 7D shows the results of staining of motile gut organoids in the same manner. The scale bar represents 50 μm. Motile gut organoids showed neuron networks with neurofilaments in the mesenchymal area; however, substantially no neurofilaments were found in non-motile gut organoids.

Figure 8A:
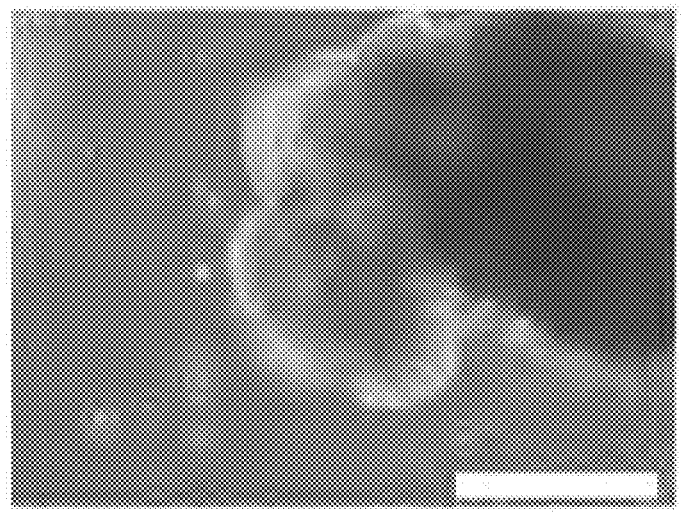

FIG. 8A shows that single organoids were transplanted on day 35 in culture under the kidney capsules of adult immunodeficient mice. The scale bar represents 200 μm.

Figure 8B:
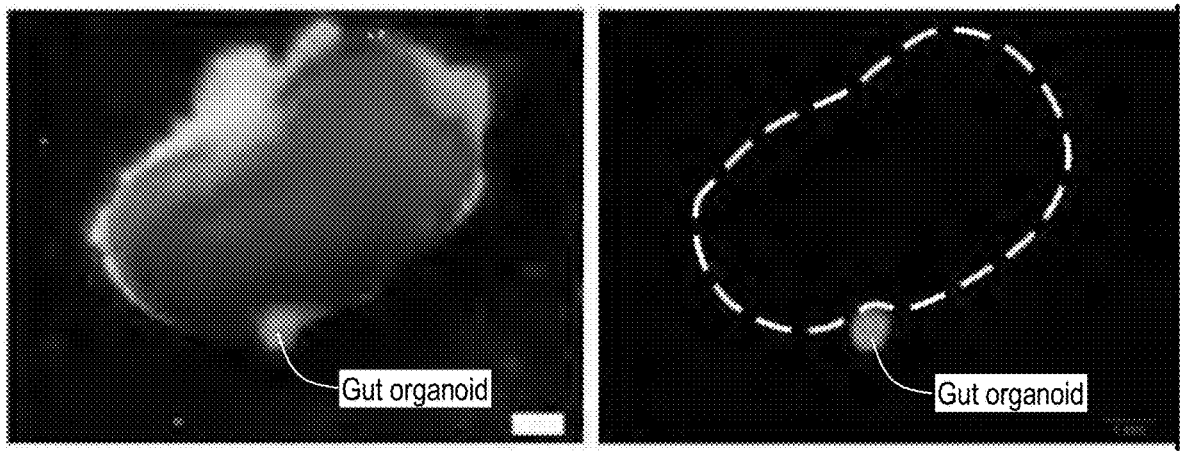

[FIG. 8B] FIG. 8B shows that constitutively EGFP-expressing organoids were present under the mouse kidney capsules 6 weeks after transplantation. The outline of mouse kidney is indicated by a dotted line in the right panel in FIG. 8B. The scale bar represents 1 mm.

Figure 8C:
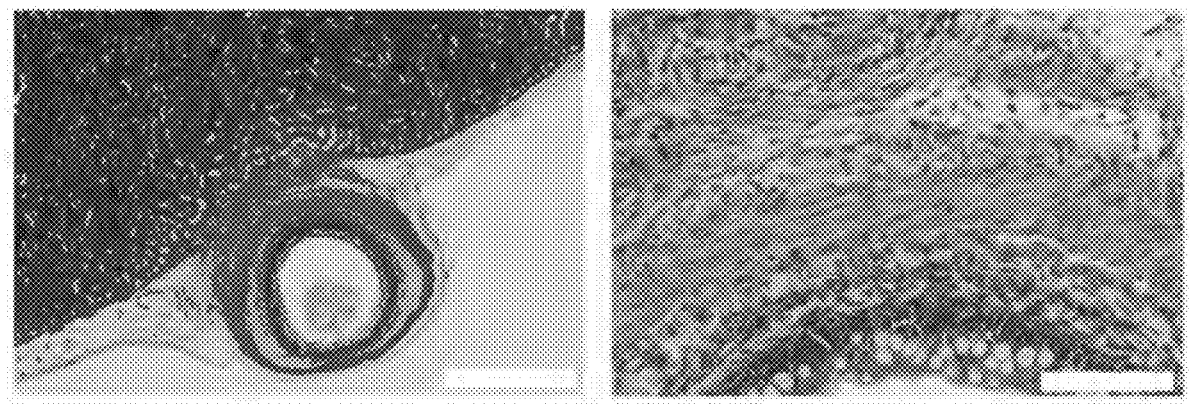

FIG. 8C shows the observation image of transplanted gut organoids stained with hematoxylin and eosin (H&E). In FIG. 8C, the scale bar in the left panel represents 500 μm, and the scale bar in the right panel represents 100 μm. Formation of lumen and laminated structures was confirmed.

Figure 8D:
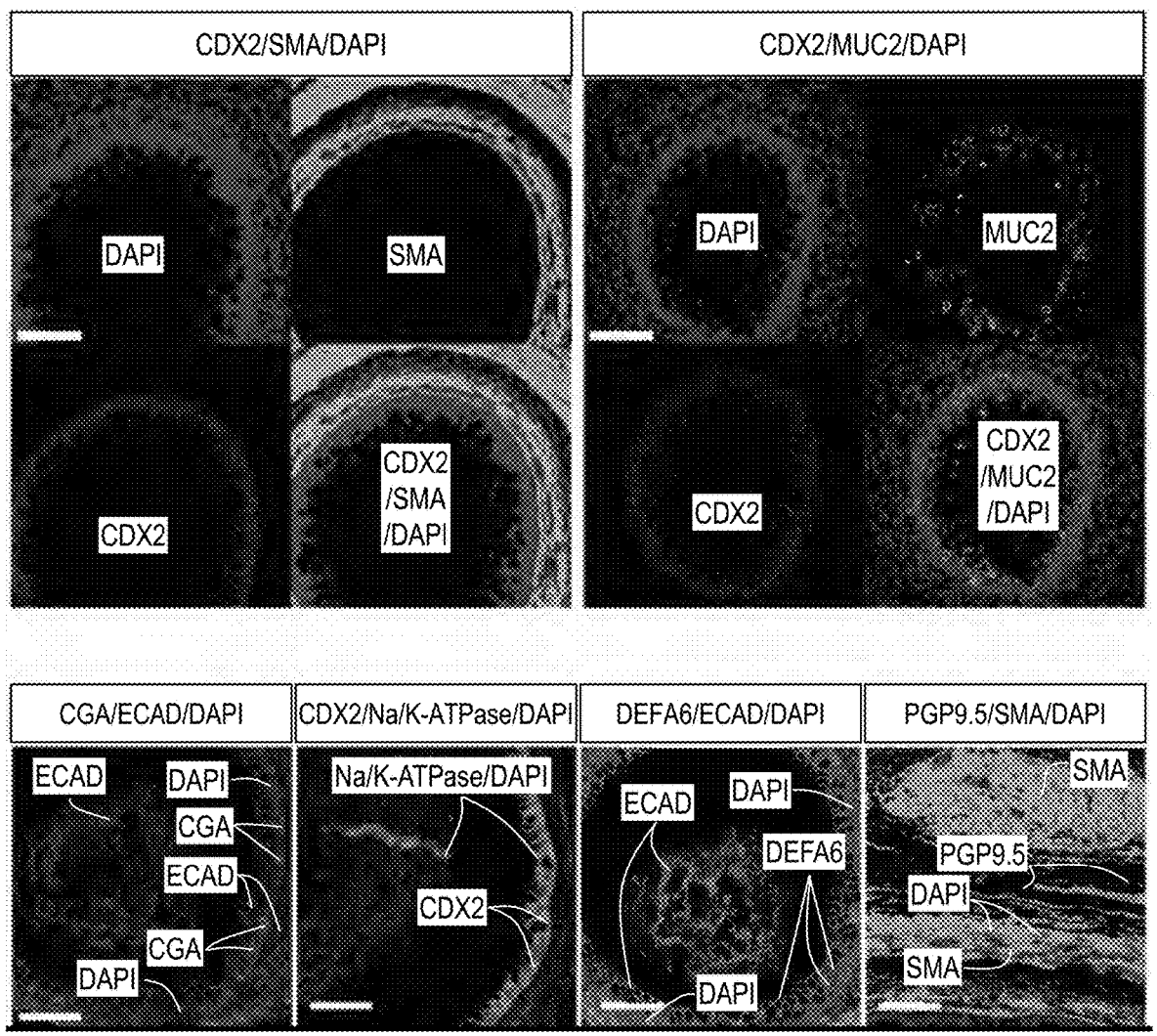

FIG. 8D shows that the transplanted gut organoids formed a laminated myenteric gut structure (α-SMA staining). MUC2 and CDX2 were expressed in the epithelial layer. The distribution of E-cadherin (ECAD) and $Na^+/K^+$-ATPase in highly differentiated enteroendocrine cells positive for chromogranin A (CGA) and Paneth cells positive for DEFA6 in the same region is shown. The expression of the neuronal marker PGP9.5 was also observed in the mesenchymal area of the smooth muscle. In FIG. 8D, the scale bar in the upper panel represents 100 and the lower panel represents 50 μm.

Figure 9A:
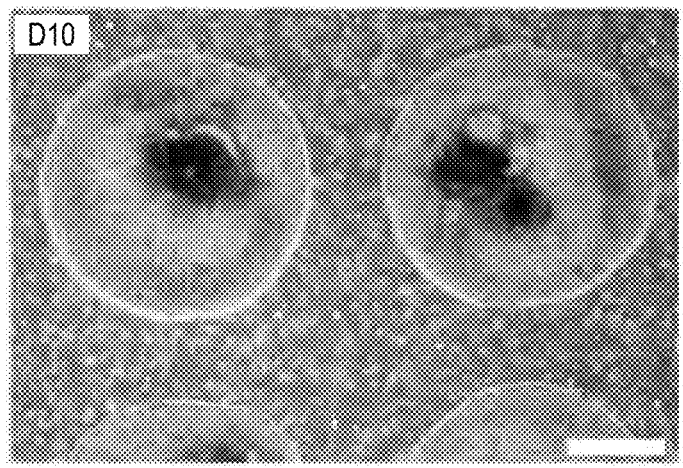

FIG. 9A indicates that human iPS cells attached and grew only within each cell-adhesive region. The scale bar represents 500 μm.

Figure 9B:
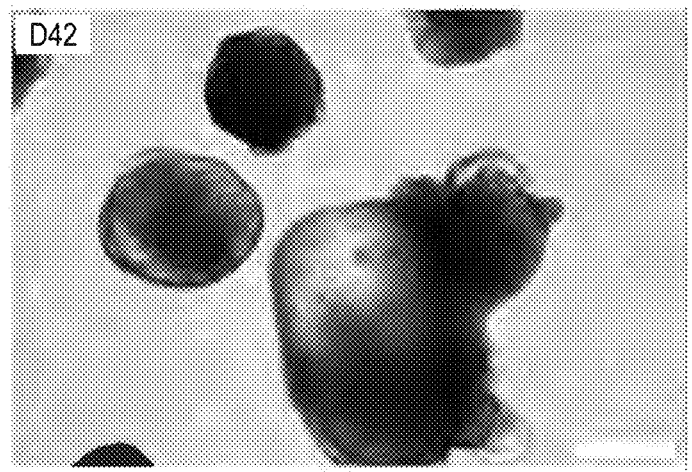

FIG. 9B indicates that day 42 gut organoids from human iPS cells formed self-assembled cystic spheroids. As with the gut organoids from human ES cells, the gut organoids from human iPS cells were also classified into simple cystic spheroids surrounded by thin cell walls or bi-component spheroids with solid and partially cystic protrusions. The scale bar represents 200

DESCRIPTION OF THE EMBODIMENTS

1. Gut Organoids

The term "gut organoid" used in an embodiment of the present invention refers to a tissue structure having functions (specifically, for example, a motile movement function, a mucus secretion function, and a substance absorption function) similar to those of an intestine of the origin organism of cells, and in particular, an intestine of a mammal such as a human or a human intestine.

The gut organoid of an embodiment of the present invention is a gut organoid derived from embryonic stem cells (ES cells) and/or induced pluripotent stem cells (iPS cells).

Embryonic stem cells (ES cells) used in an embodiment of the present invention are mammal-derived ES cells. For example, it is possible to use ES cells derived from a rodent such as a mouse or a primate such as a human. Particularly preferably, mouse- or human-derived ES cells are used. ES cells are cells of stem cell lines generated from internal cell mass belonging to a part of an embryo in the blastocyst stage that is the initial stage of animal development. ES cells can grow almost infinitely while maintaining pluripotent differentiation capacity to theoretically differentiate into all tissues. As ES cells, for example, it is possible to use cells in which a reporter gene is introduced in the vicinity of the Pdx1 gene in order to facilitate the confirmation of the degree of differentiation. For example, the 129/Sv-derived ES cell line having cells in which the LacZ gene is incorporated at the Pdx1 locus or the ES cell line SK7 Pdx1 having the GFP reporter transgene under Pdx1 promoter regulation can be used. Alternatively, it is also possible to use the ES cell line PH3 having the mRFP1 reporter transgene under Hnf3βendoderm-specific enhancer fragment regulation and the GFP reporter transgene under Pdx1 promoter regulation. It is also possible to use the ES cell lines SEES1, SEES2, SEES3, SEES4, SEES5, SEES6, and SEES7, which were generated in the Department of Cell Engineering, Department of Reproductive Biology of the National Center for Child Health and Development (NC-CHD) disclosed in Akutsu H, et al. Regen Ther. 2015;1:18-29, and cell lines obtained by introducing additional genes into these ES cell lines.

Induced pluripotent stem cells (iPS cells) used in an embodiment of the present invention are pluripotent cells obtained by reprogramming somatic cells. Production of induced pluripotent stem cells have been achieved by several groups such as the group led by Professor Shinya Yamanaka at Kyoto University, the group of Rudolf Jaenisch et al. at the Massachusetts Institute of Technology, the group of James Thomson et al. at the University of Wisconsin-Madison, and the group of Konrad Hochedlinger et al. at Harvard University. For example, International publication no. WO2007/069666 discloses nuclear reprogramming factors for somatic cells containing gene products of the Oct family gene, the Klf family gene, and the Myc family gene and nuclear reprogramming factors for somatic cells containing gene products of the Oct family gene, the Klf family gene, the Sox family gene, and the Myc family gene, and further discloses a method for producing induced pluripotent stem cells by nuclear reprogramming of somatic cells, comprising a step of bringing nuclear reprogramming factors into contact with somatic cells.

Types of somatic cells used for preparing iPS cells are not particularly limited, and arbitrary somatic cells can be used. In other words, somatic cells according to an embodiment of the present invention include all cells constituting the living body other than germ cells, and may be differentiated somatic cells or undifferentiated stem cells. The origin of somatic cells may be, but is not particularly limited to, any of mammals, birds, fish, reptiles, and amphibians. It is preferably a mammal (for example, a rodent such as a mouse or a primate such as a human) and particularly preferably a mouse or a human. In addition, in a case in which human somatic cells are used, somatic cells of either a fetus, newborn, or adult may be used. Specific examples of somatic cells include fibroblasts (e.g., skin fibroblasts), epithelial cells (e.g., gastric epithelial cells, hepatic epithelial cells, and alveolar epithelial cells), endothelial cells (e.g., blood vessel cells and lymph vessel cells), nerve cells (e.g., neurons and glial cells, pancreatic cells, blood cells, bone marrow cells, muscle cells (e.g., skeletal muscle cells, smooth muscle cells, and cardiomyocytes), hepatic parenchymal cells, nonhepatic parenchymal cells, adipocytes, osteoblasts, cells constituting periodontal tissue (e.g., periodontal ligament cells, cementoblasts, gingival fibroblasts, osteoblasts), and cells constituting the kidneys, eyes, or ears.

The term "iPS cells" refers to stem cells having long-term self-renewal ability under predetermined culture conditions (for example, under conditions for culturing ES cells) and multilineage potential capable of differentiating into ectoderm, mesoderm, and endoderm under predetermined differentiation induction conditions. In addition, iPS cells according to an embodiment of the present invention may be stem cells having ability to form a teratoma when transplanted into a test animal such as a mouse.

In order to produce iPS cells from somatic cells, first, at least one type of reprogramming gene is introduced into somatic cells. The term "reprogramming gene" refers to a gene encoding a reprogramming factor functioning to reprogramming somatic cells to iPS cells. Specific examples of a combination of reprogramming genes include, but are not limited to, the following combinations.

(i) Oct gene, Klf gene, Sox gene, Myc gene
(ii) Oct gene, Sox gene, NANOG gene, L1N28 gene
(iii) Oct gene, Klf gene, Sox gene, Myc gene, hTERT gene, SV40 largeT gene
(iv) Oct gene, Klf gene, Sox gene In one embodiment, the gut organoid has a structure enclosing a cavity. The cavity is preferably a closed cavity so that liquid can be held therein. The gut organoid enclosing a cavity is useful for evaluating drug metabolism because it can incorporate substances present outside thereof into the cavity.

In one embodiment, the gut organoid has a longitudinal length of 5 mm or more, preferably 8 mm or more, more preferably 10 mm or more, further preferably 12 mm or more, and furthermore preferably 15 mm or more. Conventionally, there has been no example in which an intestinal organoid having such a long longitudinal length has been produced, including the reports mentioned in the above "Background Art" section. A large-sized gut organoid is preferable because it can be tested more accurately than a small-sized gut organoid when used for studies to examine the effects of drugs and easily handled. For example, a large amount of liquid can be held in a cavity enclosed by a large-sized gut organoid. This makes it easy to conduct an analysis that was impossible with conventional gut organoids, in which, for example, a test drug is added to a buffer solution in which a large-sized gut organoid is suspended, the gut organoid is taken out after a certain period of time, and the liquid in the cavity is collected and analyzed. In addition, since the volume of the liquid contained in such cavity is large, a simple evaluation method such as fluorescence observation can be used without using mass spectrometry.

The term "longitudinal length" used herein refers to the longest distance when calculating a distance between two points on an outline of a gut organoid observation image, which can be connected by a single straight line passing only within the outline in the observation image, when a gut organoid in an appropriate buffer solution is observed visually or with an optical microscope. The outline of each intestinal organoid can be deformed due to motile movement; however, the maximum measurement value may be determined to be a longitudinal length.

The whole shape of the gut organoid is not particularly limited but it is usually granular. The word "granular" also encompasses "spherical."

The gut organoid preferably comprises endodermal cells, ectodermal cells, and mesodermal cells.

The endoderm forms the digestive tract and tissues of organs, such as the lung, thyroid and pancreas, and cells of secretory glands opening into the digestive tract, peritoneum, pleura, larynx, eustachian tube, trachea, bronchial tube, urinary tract (the bladder, most of the urethra, part of the ureter), and other tissues. Differentiation from ES cells or iPS cells into endodermal cells can be confirmed by measuring expression levels of endoderm-specific genes. Examples of endoderm-specific genes include AFP, SERPINA1, SST, ISL1, IPF1, IAPP, EOMES, HGF, ALBUMIN, PAX4, and TAT as well as those described later.

Particular endodermal cells that may be contained in a gut organoid include intestinal epithelial cells. The gut organoid preferably contains, as intestinal epithelial cells, at least one type of cells selected from enterocytes, goblet cells, enteroendocrine cells, and Paneth cells, and particularly preferably contain, as intestinal epithelial cells, all of enterocytes, goblet cells, enteroendocrine cells, and Paneth cells. It is possible to determine the presence of endodermal cells in a gut organoid based on the positive expression of endodermal cell markers. The enterocyte marker may be CDX2, the goblet cell marker may be MUC2, the enteroendocrine cell marker may be CGA, and the Paneth cell marker may be DEFA6. In addition to the above, ECAD, $Na^+/K^+$-ATPase, and villin are intestinal epithelial cell markers. Further, it is also possible to use the definitive endoderm markers FOXA2, SOX17, and CXCR4 as markers for detecting endodermal cells. The primary endoderm and mesoderm markers GATA4, GATA6, and T (Brachyury) also can be used as markers for detecting endodermal cells.

The ectoderm forms several tissues including, for example, skin epidermis, epithelium of the urethral end of a man, hair, nails, skin glands (including mammary gland and sweat gland), sensory organs (oral cavity, pharynx, nose, epithelium at the distal end of the rectum, salivary gland) and lens,. A part of the ectoderm is invaginated in a groove shape in the developmental process to form a neural tube, which is also a source of neurons and melanocytes of the central nervous system such as the brain and spinal cord. The ectoderm also forms the peripheral nervous system. Differentiation from ES cells or iPS cells into ectodermal cells can be confirmed by measuring expression levels of ectoderm-specific genes. Examples of ectoderm-specific genes may include β-TUBLIN, NESTIN, GALANIN, GCM1, GFAP, NEUROD1, OLIG2, SYNAPTPHYSIN, DESMIN, and TH as well as those described later.

Particular ectodermal cells that may be contained in a gut organoid include cells that constitute the intestinal nerve plexus. It is possible to determine the presence of ectodermal cells in a gut organoid based on the positive expression of ectodermal cell markers. As markers for detecting ectodermal cells, the intestinal nerve plexus marker PGP9.5 and the neural progenitor marker SOX1 can be used.

The mesoderm forms a body cavity and mesothelium lining inside thereof, muscles, skeletons, skin dermis, connective tissue, heart, blood vessels (including vascular endothelium), blood (including blood cells), lymph vessels, spleen, kidneys, ureters, and gonad (testis, uterus, and gonadal epithelium). Differentiation from ES cells or iPS cells into mesodermal cells can be confirmed by measuring expression levels of mesoderm-specific genes. Examples of mesoderm-specific genes may include FLK-1, COL2A1, FLT1, HBZ, MYF5, MYOD1, RUNX2, and PECAM1 as well as those described later.

Particular mesodermal cells that may be contained in a gut organoid include smooth muscle cells and interstitial cells of Cajal. It is possible to determine the presence of mesodermal cells in gut organoids based on the positive expression of mesodermal cell markers. As mesodermal cell markers, the smooth muscle cell marker α-smooth muscle actin (SMA) and the Cajal cell markers CD34 and CKIT (for double-positive cells) can be used. The primary endoderm and mesoderm markers GATA4, GATA6, and T (Brachyury) also can be used as markers for detecting mesodermal cells.

The gut organoid further preferably contains intestine stem cells. It is possible to determine the presence of intestine stem cells based on the positivity of the intestine stem cell marker LGR5.

The gut organoid preferably further contains serotonin-positive enteroendocrine cells.

The gut organoid preferably further contains transporter-positive cells and can absorb substances via transporters. Examples of a transporter include the intestine oligopeptide transporter (PEPT1) and the ATP-binding cassette (ABC) transporters ABCB1 and ABCG2.

The gut organoid preferably further contains cystic fibrosis conductance regulator (CFTR)-positive intestinal epithelial cells. CFTR-positive intestinal epithelial cells are involved in secretion of mucus. In other words, the gut organoid having CFTR-positive intestinal epithelial cells has gut-like mucus secretion ability.

The gut organoid preferably further contains histamine H1 receptor-positive cells.

The gut organoid of an embodiment of the present invention preferably contains intestinal epithelial cells in at least a part of the outer surface thereof. According to this embodiment, substances outside of the gut organoid can be absorbed into the cavity via intestinal epithelial cells on the outer surface thereof, which is preferable. In addition, in this embodiment, when intestinal epithelial cells on the outer surface are transporter-positive, it allows uptake of substances via transporters, which is further preferable. In other words, the gut organoid containing transporter-positive intestinal epithelial cells has gut-like substance absorption ability. Note that in the mammalian intestine, intestinal epithelial cells are facing the inside of the intestinal tract which is hollow, which makes a difference from the gut organoid in this embodiment.

More preferably, the gut organoid of an embodiment of the present invention is observed with the development of microvilli and crypt on the outer surface.

The gut organoid of an embodiment of the present invention preferably has ability to perform contractile movement similar to motile movement. Such function results from the development of neural networks and smooth muscles. In the following description, the ability to perform contractile movement similar to peristaltic movement is sometimes referred to as "contractile activity/movement." A motile gut organoid particularly preferably shows gut-like drug responsiveness, indicating that the frequency of contraction is increased by histamine treatment and the frequency of contraction is decreased by atropine treatment. The motile gut organoid showing gut-like drug responsiveness can be appropriately used for evaluating influence of drugs on peristaltic movement of the intestine.

As described above, the gut organoid of an embodiment of the present invention has a sufficient size and gut-like functions and can absorb substances from outside into its enclosing cavity. Therefore, it is useful for the development of drugs for preventing or treating intestinal diseases and pathological studies on intestinal diseases. When using the gut organoid of an embodiment of the present invention, there is no need to conduct labor-consuming steps of forming a breakable single layer film on a semi-permeable membrane in, for example, a conventional drug test method using Caco-2 and measuring transepithelial electrical resistance (TEER) to indicate membrane integrity.

In addition, production of the gut organoid of an embodiment of the present invention from disease-specific iPS cells facilitates research on intestinal diseases involving genetic factors and evaluation of drugs.

2. Method for producing gut organoids

The gut organoid of an embodiment of the present invention can be produced by a method comprising the following steps:

step 1 of plating cells selected from embryonic stem cells and induced pluripotent stem cells on a cell culture substrate comprising a substrate having a surface on which cell-adhesive regions and a non-cell-adhesive region surrounding the cell-adhesive regions are formed; and step 2 of culturing cells plated in step 1.

Cells selected from embryonic stem cells and induced pluripotent stem cells used in this method are described above.

A preferred embodiment of a cell culture substrate used in an embodiment of the present invention is described below.

Preferably, cell-adhesive regions are present in the form of multiple islands within a non-cell-adhesive region on a cell culture substrate used in an embodiment of the present invention.

Preferably, a non-cell-adhesive region is formed by immobilizing polyethylene glycol on a cell culture substrate used in an embodiment of the present invention, and cell-adhesive regions are formed by oxidizing and/or decomposing at least one part of polyethylene glycol immobilized on the substrate.

According to an embodiment of the present invention, the term "cell adhesiveness" means the strength of adhering cells, that is to say, the ease of cell adhesion. The term "cell-adhesive region" refers to a region with favorable cell adhesiveness, and the term "non-cell-adhesive region" refers to a region with poor cell adhesiveness. Accordingly, when cells are plated on a substrate with a pattern of cell-adhesive regions surrounded by a non-cell-adhesive region, cells adhere to the cell-adhesive regions but not to the non-cell-adhesive region, allowing the cells to be arranged in such pattern on the surface of the cell culture substrate.

As an indicator for judging cell adhesiveness, the cell adhesion/spreading rate when actually culturing cells can be used. A cell-adhesive surface is preferably a surface having a cell adhesion/spreading rate of 60% or more and more preferably a surface having a cell adhesion/spreading rate of 80% or more. When the cell adhesion/spreading rate is high, cells can be cultured efficiently. The cell adhesion/spreading rate according to an embodiment of the present invention can be defined as a proportion of adhering/spread cells at a time point when cells to be cultured at a plating density in a range of 4000 cells/cm$^2$ to less than 30000 cells/cm$^2$ have been plated on a surface of a measurement subject, stored in an incubator at 37° C. and a $CO_2$ concentration of 5%, and cultured for 14.5 hours ({(the number of adhering cells)/(the number of plated cells)}×100(%)).

In the above measurement, cell plating is conducted in a manner such that cells suspended in a 10% FBS-containing DMEM medium are plated on a measurement subject, and then, the measurement subject on which cells have been plated is slowly shaken to allow the cells to be distribute as uniformly as possible. Further, the cell adhesion/spreading rate is measured after changing the medium immediately before the measurement to remove non-adhering cells. Upon measurement of the cell adhesion/spreading rate, areas other than areas where the cell presence density is likely to be specific (for example, the center of a predetermined area where the presence density tends to be high and the periphery of a predetermined area where the presence density tends to be low) are determined to be measurement areas.

Meanwhile, the term "non-cell adhesiveness" refers to the property that makes cells difficult to adhere. Non-cell adhesiveness is determined whether or not cell adhesion or spreading is likely to occur depending on properties such as chemical properties and physical properties of a surface. A non-cell-adhesive surface is a surface having a cell adhesion/spreading rate (defined above) of preferably less than 60%, more preferably less than 40%, further preferably 5% or less, and most preferably 2% or less.

Preferably, a non-cell-adhesive region is formed by immobilizing polyethylene glycol on a cell culture substrate used in an embodiment of the present invention, and cell-adhesive regions are formed by oxidizing and/or decomposing at least one part of polyethylene glycol immobilized on the substrate. Such a cell culture substrate can be produced by, for example, forming a thin film of polyethylene glycol (PEG) on the whole surface of a substrate, and then, applying oxidation treatment and/or decomposition treatment to an area where cell adhesion is desired so as to impart cell adhesiveness. An area to which the treatment is not applied is designated to be a non-cell-adhesive region on which PEG is immobilized.

Polyethylene glycol (PEG) includes at least an ethylene glycol chain (EG chain) comprising at least one ethylene glycol unit (($CH_2)_2$—O), which may be either linear or branched chain. The ethylene glycol chain has a structure expressed by, for example, the following formula:

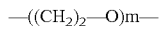

—(($CH_2)_2$—O)m—

(m is an integer indicating the degree of polymerization). m is preferably an integer of 1 to 13 and more preferably an integer of 1 to 10.

PEG also includes ethylene glycol oligomer. In addition, PEG may be functional-group-containing PEG. Examples of a functional group include an epoxy group, a carboxyl group, an N-hydroxysuccinimide group, a carbodiimide group, an amino group, a glutaraldehyde group, and a (meth)acryloyl group. A functional group is optionally introduced via a linker, preferably at the end of the chain. Examples of functional-group-containing PEG include PEG (meth)acrylate and PEG di(meth)acrylate.

A substrate used for a cell culture substrate is not particularly limited as long as it is formed with a material that allows formation of a PEG thin film on the surface thereof. Specific examples of a substrate include: inorganic materials such as a metal, glass, ceramic, and silicon; and organic materials represented by elastomers and plastics (e.g., polystyrene resin, polyester resin, polyethylene resin, polypropylene resin, ABS resin, nylon, acrylic resin, fluororesin, polycarbonate resin, polyurethane resin, methylpentene resin, phenol resin, melamine resin, epoxy resin, and vinyl chloride resin). The shape of a substrate is also not limited, and examples thereof include a flat shape such as a flat substrate, a flat membrane, a film, or a porous membrane, and a three-dimensional shape such as a cylinder, a stamp, a multi-well substrate, or a micro flow path. When a film is used, the thickness thereof is not particularly limited. However, it is usually 0.1 to 1000 μm, preferably 1 to 500 μm, and more preferably 10 to 200 μm.

The average thickness of the PEG thin film formed on a substrate is preferably 0.8 nm to 500 μm, more preferably 0.8 nm to 100 μm, further preferably 1 nm to 10 μm, and most preferably 1.5 nm to 1μm. In a case in which the average thickness is 0.8 nm or more, protein adsorption and cell adhesion are unlikely to be affected by areas other than areas covered with a PEG thin film on the substrate surface, which is preferable. In addition, in a case in which the average thickness is 500 μm or less, coating is relatively easy. Further, by making the thickness of the PEG thin film equal to or larger than a certain value, it is possible to inhibit adhesion and spreading of cells to a region other than a cell-adhesive region. In addition, by making the thickness of the PEG thin film equal to or smaller than a certain value, it is also possible to distribute factors necessary for cell survival contained in a culture solution to cells close to the substrate in a cell-adhesive region.

Examples of a method for forming a PEG thin film on a substrate surface include a method for directly adsorbing PEG to a substrate, a method for directly coating PEG on a substrate, a method in which a substrate is coated with PEG and then subjected to a crosslinking treatment, a method in which an underlayer is formed on a substrate in order to enhance adhesion to a substrate and then the substrate is coated with PEG, and a method for forming a polymerization initiation point on the surface of a substrate and then polymerizing PEG. A method for forming an underlayer on a substrate and then coating the substrate with PEG is preferable.

An underlayer can be formed by, for example, the method disclosed in JP Patent Publication (Kokai) No. 2012-175983 A. Preferably, an underlayer is formed using a silane coupling agent containing a functional group capable of reacting with a hydroxyl group or a functional group introduced at the end of PEG terminal to form a covalent bond or a functional group that can be converted to such functional group. Examples of such functional groups include a (meth)acryloyl group, a (1H-imidazol-1-yl) carbonyl group, a succinimidyloxycarbonyl group, a glycidyl group, an epoxy group, an aldehyde group, an amino group, a thiol group, a carboxyl group, an azide group, a cyano group, an active ester group (such as a 1H-benzotriazole-1-yloxycarbonyl group, a pentafluorophenyloxycarbonyl group, or a para-nitrophenyloxycarbonyl group), a halogenated carbonyl group, an isocyanate group, and a maleimide group. Of these, a (meth)acryloyl group, glycidyl group or epoxy group is preferable and a glycidyl group or epoxy group is most preferable.

For example, in one example of a silane coupling agent having a terminal methacryloyl group (methacryloyl silane), the water contact angle on the substrate surface to which methacryloylsilane has been added is typically 45° or more, desirably 47° or more, more desirably 48° or more, and further desirably 50° or more. Thus, a sufficient non-cell-adhesive region can be formed by subsequently immobilizing PEG.

The density of PEG immobilized on the substrate and non-cell adhesiveness can be readily evaluated based on the water contact angle on the surface. For example, when the water contact angle after PEG immobilization is typically 48° or less, preferably 40° or less, more preferably 30° or less, it is thought that PEG is present at a sufficient density, and therefore, non-cell adhesiveness is achieved. Note that the water contact angle according to an embodiment of the present invention means a water contact angle measured at 23° C.

According to an embodiment of the present invention, the word "oxidation" has a narrow meaning and refers to a reaction in which an organic compound, that is to say, PEG, reacts with oxygen and the content of oxygen becomes larger than that before the reaction. According to an embodiment of the present invention, the word "decomposition" refers to a reaction in which a bond of an organic compound, that is to say, PEG, is cleaved. Typically, "decomposition" is caused by, but is not limited to, oxidation, ultraviolet irradiation, or other treatments. In a case in which "decomposition" is accompanied by oxidation (i.e., oxidation decomposition), "decomposition" and "oxidation" refers to the same treatment.

Decomposition by ultraviolet irradiation means that PEG absorbs ultraviolet rays and decomposes via an excited state. When a system in which PEG is present together with molecular species containing oxygen (e.g., oxygen or water) with ultraviolet rays, ultraviolet rays are absorbed by PEG and decomposition occurs, and in some cases, the molecular species is activated to react with PEG. The latter reaction can be classified as "oxidation." A reaction in which PEG is decomposed via oxidation caused by the activated molecular species can be classified as "decomposition by oxidation" rather than "decomposition by ultraviolet irradiation." As described above, "oxidation" and "decomposition" may be duplicated as operations, and therefore, they cannot be distinguished clearly. In view of this, the term "oxidation and/or decomposition" is used herein.

Examples of an oxidation and/or decomposition method include a method for irradiating a PEG thin film with ultraviolet rays, a method for treating a PEG thin film with a photocatalyst, and a method for treating a PEG thin film with an oxidizing agent. In a case in which a PEG thin film is partially oxidized and/or decomposed, a mask such as a photomask or a stencil mask may be used or a stamp may be used. In addition, oxidation and/or decomposition may be carried out by a direct drawing method such as a method using laser such as ultraviolet laser.

In the case of ultraviolet irradiation treatment, it is preferable to use, as a light source, a lamp that emits ultraviolet rays in the region ranging from the VUV region to the UV-C region such as a mercury lamp that emits ultraviolet rays with a wavelength of 185 nm or 254 nm or an excimer lamp that emits ultraviolet rays with a wavelength of 172 nm. In the case of photocatalyst treatment, it is preferable to use a light source that emits ultraviolet rays with a wavelength of 365 nm or less and more preferably a light source that emits ultraviolet rays with a wavelength of 254 nm or less. As a photocatalyst, a titanium oxide photocatalyst, including a titanium oxide photocatalyst activated with a metal ion or metal colloid, is preferably used. As an oxidizing agent, an organic acid or an inorganic acid can be used without any particular limitation; however, since a high concentration acid is difficult to handle, it may be diluted to a concentration of 10% or less before use. The optimum ultraviolet treatment time, photocatalyst treatment time, or oxidizing agent treatment time can be appropriately determined according to various conditions such as the ultraviolet intensity of the light source used, the activity of the photocatalyst, the oxidizing power and concentration of the oxidizing agent.

The amount of carbon in a cell-adhesive region (including an underlayer when there is an underlayer) is preferably lower than the amount of carbon in a non-cell-adhesive region (including an underlayer when there is an underlayer). Specifically, the amount of carbon in a cell-adhesive region is 20% to 99% of the amount of carbon in a non-cell-adhesive region. In addition, the proportion of carbon bonded to oxygen (%) with respect to carbon present in a cell-adhesive region (including an underlayer when there is an underlayer) is preferably smaller than the proportion of carbon bonded to oxygen (%) with respect to carbon present in a non-cell-adhesive region (including an underlayer when there is an underlayer). Specifically, the proportion of carbon bonded to oxygen (%) with respect to carbon present in a cell-adhesive region is preferably 35% to 99% of the proportion of carbon bonded to oxygen (%) with respect to carbon present in a non-cell-adhesive region. Along with an increase in the ultraviolet exposure amount during patterning, cell adhesiveness increases. This is because a high level of adhesiveness at the time of cell collection causes cells not to be easily peeled off, thereby making it difficult to collect the cells.

According to an embodiment of the present invention, "the amount of carbon" is defined as "the amount of carbon calculated from the analysis value of the C1s peak obtained by using an X-ray photoelectron spectrometer" and "the proportion of carbon bonded to oxygen" is defined as "the proportion of carbon bonded to oxygen calculated from the analysis value of the C1s peak obtained by using an X-ray photoelectron spectrometer."

The area of each cell-adhesive region on a cell culture substrate used in an embodiment of the present invention is not particularly limited. Specifically, an example of the area of each cell-adhesive region upon pattern formation is 0.1 mm$^2$ or more, preferably 0.5 mm$^2$ or more, preferably 0.785 mm$^2$ or more, more preferably 1.0 mm$^2$ or more, further preferably 1.2 mm$^2$ or more, furthermore preferably 1.5 mm$^2$ or more, most preferably 1.7 mm$^2$ or more while it is preferably 25 mm$^2$ or less, more preferably 15 mm$^2$ or less, further preferably 10 mm$^2$ or less, and most preferably 5 mm$^2$ or less. When the area of each cell-adhesive region falls within the above range, a large-sized gut organoid having a longitudinal length exceeding 5 mm can be easily cultured.

The shape of each cell-adhesive region is not particularly limited. However, it may be a polygonal shape such as a rectangular, circular, or oblong shape. A circular cell-adhesive region is preferable. The diameter of a circular cell-adhesive region is preferably a diameter satisfying the above area range. Specifically, the diameter of a circular cell-adhesive region is, for example, 0.35 mm or more, preferably 0.8 mm or more, more preferably 1.0 mm or more, further preferably 1.2 mm or more, and furthermore preferably 1.5 mm or more, while it is preferably 6 mm or less, more preferably 4 mm or less, further preferably 3 mm, and furthermore preferably 2 mm or less. Each of cell-adhesive regions present on a single cell culture substrate preferably has the same area, and more preferably has the same area and shape, while cell-adhesive regions having different areas and shapes may be present.

In addition, each cell-adhesive region is surrounded by a non-cell-adhesive region on a cell culture substrate. Specifically, cell-adhesive regions are isolated from each other and arranged apart from each other with a distance of preferably 0.75 mm or more and more preferably 1.5 mm or more. In other words, cell-adhesive regions are arranged such that the shortest distance between cell-adhesive regions (in the case of a circle, the distance between the centers of two circles is the sum of the radiuses plus the above value) is preferably 0.75 mm or more and more preferably 1.5 mm or more. By arranging cell-adhesive regions to be apart from each other with not less than a certain distance, cells within a cell-adhesive region are uniformly cultured with a certain distance from each of other cell-adhesive regions without forming intercellular bonds with cells in other cell-adhesive regions, thereby making it possible to construct a culture system with high reproducibility.

The proportion of cell-adhesive regions on a cell culture substrate is usually 5% to 80%, preferably 20% to 70%, and more preferably 40% to 60%. Even in a case in which a substrate is placed in a dish or other types of containers, this proportion is defined as the proportion of cell-adhesive regions with respect to the entire substrate (not with respect to the bottom of the container). Cell death can be prevented by setting the amount of cells to a culture solution to not less than a certain value, making it possible to prevent exhaustion of factors necessary for survival and damage to cells.

In addition, it is preferable that cell-adhesive regions are regularly arranged at certain intervals in, for example, a lattice pattern at the same pitch in the longitudinal and lateral directions. By maintaining the paracrine effects of a product produced from cells in each cell-adhesive region at a constant level, the influence on differentiation can be made constant.

For example, a pattern having a plurality of circular cell-adhesive regions can be formed by using a photomask having a plurality of circular openings, disposing a glass substrate on which a PEG thin film has been formed and the photomask such that they face each other, and emitting ultraviolet rays from the photomask side, thereby oxidizing a region corresponding to each opening of the photomask on the PEG thin film.

A cell culture substrate used in an embodiment of the present invention is preferably subjected to precoating treatment in order to promote adhesion of embryonic stem cells (ES cells) and/or induced pluripotent stem cells (iPS cells) to cell-adhesive regions. Precoating treatment can be performed by coating a cell culture substrate with an extracellular matrix (collagen, fibronectin, proteoglycan, laminin, or vitronectin), gelatin, lysine, a peptide, or a gel matrix containing any thereof, serum, or other substances. By performing precoating treatment, it is possible to promote adhesion of ES cells and iPS cells having low adhesiveness to cell-adhesive regions and effectively carry out adhesion culture and differentiation induction of cells.

Similarly, in order to promote adhesion of ES cells or iPS cells to cell-adhesive regions, it is preferable to plate and culture feeder cells for about 24 hours before plating ES cells or iPS cells, and then, culture ES cells or iPS cells on the feeder cells. Feeder cells that are usually used in the art can be used without particular limitations; however, for example, fibroblasts can be used. Feeder cells are plated on a cell culture substrate at a density of less than $1.26 \times 10^5$ cells/cm$^2$, which is preferably a density of $6.3 \times 10^4$ cells/cm$^2$ or less but $3.15 \times 10^4$ cells/cm$^2$ or more.

According to an embodiment of the present invention, it is possible to carry out both precoating treatment and plating of feeder cells. It is also possible to carry out precoating treatment alone or plating of feeder cells alone without precoating treatment.

According to the method for producing a gut organoid of an embodiment of the present invention, a gut organoid can be readily produced from cells selected from embryonic stem cells and induced pluripotent stem cells.

Hereinafter, steps 1 and 2 of the method for producing a gut organoid of an embodiment of the present invention will be described.

In step 1, embryonic stem cells and/or induced pluripotent stem cells to be plated on a cell culture substrate are designated to be cells which have been treated using a non-differentiation induction medium so as to remain undifferentiated. The medium is switched to a differentiation induction medium immediately before plating on a cell culture substrate surface, and the stem cells are plated on the substrate surface.

Such non-differentiation induction medium is not particularly limited as long as it is a medium that does not allow differentiation induction of embryonic stem cells and/or induced pluripotent stem cells. However, for example, it may be a medium containing a leukemia inhibitory factor known to have a feature of allowing mouse embryonic stem cells and mouse induced pluripotent stem cells to remain undifferentiated.

In step 1, the plating density of embryonic stem cells and/or induced pluripotent stem cells on a cell culture substrate is not particularly limited as long as it complies with an ordinary method. In one embodiment of an embodiment of the present invention, embryonic stem cells and/or induced pluripotent stem cells are plated on a cell culture substrate at a density of preferably $3 \times 10^4$ cells/cm$^2$ or more, more preferably $3 \times 10^4$ to $5 \times 10^5$ cells/cm$^2$, and further preferably $3 \cdot 10^4$ to $2.5 \times 10^5$ cells/cm$^2$.

Step 2 is a step of culturing cells plated in step 1.

The culture temperature in step 2 is usually 37° C. It is preferable to carry out the culture under a $CO_2$ concentration atmosphere of about 5% by using an appropriate cell culture apparatus such as a $CO_2$ cell culture apparatus.

Step 2 is conducted in a differentiation induction medium. A differentiation induction medium is not particularly limited as long as it is a medium that allows differentiation induction of embryonic stem cells and/or induced pluripotent stem cells. A serum-containing medium, and a serum-free medium containing a known component having a property of replacing serum can be used. It is possible to use MEM medium, BME medium, DMEM medium, DMEM-F12 medium, αMEM medium, IMDM medium, ES medium, DM-160 medium, Fisher medium, F12 medium, WE medium, and RPMI1640 medium depending on the type of cells used. It is also possible to add various growth factors, antibiotics, amino acids, and other additives to a medium. Examples thereof include 0.05 mM to 1.0 mM nonessential amino acids, 1 mM to 5 mM GlutaMAX-I, 0.01 mM to 0.1 mM β-mercaptoethanol, 0.1 mM to 2 mM pyruvic acid, 10 U/ml to 200 U/ml penicillin, 10 μg/ml to 200 μg/ml streptomycin, 10 m/ml to 200 m/ml L-ascorbic acid 2-phosphate, and a 1μM to 20 μM ROCK inhibitor (e.g., Y-27632).

When cells are cultured in a differentiation induction medium in step 2, cells become confluent in cell-adhesive regions within about 3 days after plating, resulting in formation of a cell pattern. Thereafter, cells are further cultured. Accordingly, the cell pattern has become a cell mass raised in a hemispheric dome-like shape on each cell-adhesive region, and differentiation proceeds in the cell mass. The cell mass is detached from each cell-adhesive region within about 30 days after plating and suspended in a medium. The gut organoid of an embodiment of the present invention can be obtained by further continuing culture of the floating cell mass if needed. The culture period is not particularly limited, and the culture may be terminated at the stage of detachment from the cell-adhesive region, but typically the culture is performed from 30 days to 130 days after plating. The medium is changed as necessary during this period. Unlike the method disclosed in Non Patent Literature 1, according to the method of an embodiment of the present invention, as differentiation proceeds autonomously in the cell mass such that the cell mass turns into a gut organoid, the procedure is simple and the obtained gut organoid is considered to have a function close to the function of the natural intestine, which is preferable.

In one preferred embodiment, step 2 includes:
inducing differentiation of a part of the cells plated in step 1 into endodermal cells; and
inducing differentiation of another part of the cells plated in step 1 into ectodermal cells.

In this embodiment, more preferably, the differentiation of the part of the cells plated in step 1 into endodermal cells is induced before the differentiation of the another part of the cells plated in the step 1 into ectodermal cells in the step 2. In embryogenesis in its natural state, an intestinal structure is formed first and then nerve cells invade to develop the intestinal nervous system. Accordingly, as in the case of this embodiment, an epithelial system structure such as intestinal epithelium derived from the endoderm is formed due to advancement of differentiation into endodermal cells, and then, differentiation into ectodermal cells proceeds and the nervous system derived from the ectoderm develops. This is considered to be a process of mimicking the development mechanism. Therefore, the method for producing a gut organoid in this embodiment is expected to be used for studies on elucidation of the mechanism of nervous system development in the intestine. In addition, since a gut organoid obtained by this method is a gut organoid that underwent a process similar to the process of natural occurrence, its drug response is considered to be closer to the in vivo drug response. Therefore, such gut organoid can be expected to be a suitable model for drug discovery research.

It is possible to confirm that the timing of the differentiation of the part of the cells plated in step 1 into endodermal cells is earlier than the timing of the differentiation of the another part of the cells plated in step 1 into ectodermal cells in step 2 based on the condition that the timing at which the increment per unit time of the expression level of the endoderm marker in the cell culture is maximized is earlier than the timing at which the increment per unit time of the expression level of the ectoderm marker is maximized. In this case, the endoderm marker may be an endoderm-specific gene. Specific examples thereof include the germ endoderm markers FOXA2, SOX17, and CXCR4. The ectoderm marker may be an ectoderm-specific gene. Specific examples thereof include the neural progenitor marker SOX1. The expression level of each marker in the cell culture can be indicated as the relative value of its mRNA expression level with respect to the mRNA expression level of GAPDH. The increment per week can be employed as the increment per unit time. Specifically, by measuring the expression level of each marker at 1-week intervals after plating, it is possible to know the weekly increment of the expression level.

In this embodiment, more preferably, step 2 includes inducing the differentiation of the part of the cells plated in step 1 into endodermal cells within 14 days after plating. Specifically, the time period in which the increment per unit time of the expression level of the endoderm marker in the cell culture is maximized is between plating and day 14 after plating. When differentiation into endodermal cells is induced during this period, it facilitates obtaining a gut organoid having gut-like functions. Even in such case, cells that differentiate into endodermal cells on day 15 or later after plating may exist. However, it is preferable that most of the cells differentiate into endodermal cells within 14 days after plating.

In this embodiment, more preferably, step 2 includes inducing the differentiation of the another part of the cells plated in step 1 into ectodermal cells on day 15 or later after plating. Specifically, the timing at which the increment per unit time of the expression level of the ectoderm marker in the cell culture is maximized is on day 15 or later after plating. When differentiation into ectodermal cells is induced at this timing, it facilitates obtaining a gut organoid having gut-like functions. Even in such case, cells that differentiate into ectodermal cells within 14 days after plating may exist. However, it is preferable that most of the cells differentiate into ectodermal cells on day 15 or later after plating.

In another preferred embodiment of step 2, the differentiation induction medium does not contain components (xenogeneic-derived components) derived from a mammal, the species of which is different from the species of the mammal of cells to be cultured. Examples of a medium free of xenogeneic-derived components include a serum-free medium containing known components having alternative serum properties. A gut organoid that has differentiated in a medium free of xenogeneic-derived components is highly safe upon in vivo transplantation and therefore appropriate for regenerative medicine.

In another preferred embodiment of step 2, the differentiation induction medium further contains an insulin-like growth factor (IGF) and a basic fibroblast growth factor (bFGF). Surprisingly, the present inventors found that when embryonic stem cells and/or induced pluripotent stem cells are cultured in the differentiation induction medium containing these two components, a gut organoid characterized by having a structure enclosing a cavity and having a longitudinal length of 5 mm or more and preferably further comprising the above preferred features can be produced. IGF is particularly preferably IGF-1. The IGF concentration in the differentiation induction medium is preferably 20 ng/ml to 2μg/ml. The bFGF concentration in the differentiation induction medium is preferably 2 ng/ml to 200 ng/ml. Preferably, IGF and bFGF are from the same species as cells to be cultured. In addition, IGF and bFGF are not limited to those comprising natural amino acid sequences, and may be functionally equivalent mutants or fragments. For example, LONG R3-IGF-1 (Sigma-Aldrich) can be used as IGF-1. Particularly preferably, the differentiation induction medium further contain heregulin as well as IGF and bFGF. Heregulin is preferably heregulin-1β. Heregulin-1β may at least contain an EGF domain. The heregulin concentration in the differentiation induction medium is preferably 1 ng/ml to 100 ng/ml. In addition, in a case in which the differentiation induction medium contains heregulin, heregulin is preferably from the same species as cells to be cultured, and is not limited to those comprising natural amino acid sequences, and may be a functionally equivalent mutant or fragment.

In an embodiment in which differentiation into a gut organoid is induced using a differentiation induction medium containing IGF and bFGF in step 2, the differentiation induction medium does not necessarily contain IGF and bFGF at the timing of plating in step 1. For example, in step 1, it is possible to plate cells on a cell culture substrate and culture the cells in a differentiation induction medium free of IGF and bFGF until the cells become confluent in cell-adhesive regions (for, for example, about 3 days after plating), replace the medium with a differentiation induction medium containing IGF and bFGF after the cells have become confluent, and further continue the culture.

3. Differentiation Induction Medium for Producing Gut Organoid and Kit for Producing Gut Organoid An embodiment of the present invention also provides a differentiation induction medium for producing a gut organoid, which contains IGF and bFGF.

This differentiation induction medium for producing a gut organoid will be described below in detail.

When embryonic stem cells and/or induced pluripotent stem cells are cultured in the differentiation induction medium containing for producing a gut organoid, a gut organoid characterized by having a structure enclosing a cavity and a longitudinal length of 5 mm or more, and preferably, further comprising the above preferred features can be produced.

An embodiment of the present invention also relates to a kit for producing a gut organoid, comprising the above-described differentiation induction medium for producing a gut organoid and a cell culture substrate comprising a substrate having a surface on which cell-adhesive regions and a non-cell-adhesive region surrounding the cell-adhesive regions are formed.

The cell culture substrate in this kit is described above regarding the method for producing a gut organoid.

The differentiation induction medium and kit of an embodiment of the present invention are useful for producing gut organoids.

Hereinafter, an embodiment of the present invention will be described with reference to concrete experimental results, but the scope of an embodiment of the present invention is not limited to the scope of the experimental results.

EXAMPLES

1. Production of Cell Culture Substrate (First Stage Reaction)

Toluene in an amount of 58.5 g and epoxysilane TSL8350 (manufactured by MPM Holdings Inc.) in an amount of 20.25 g were mixed, the resulting liquid mixture was stirred, during which a catalytic amount of triethylamine was added, and the mixture was further stirred at room temperature for several minutes. A 5-inch square glass substrate, which was previously UV-cleaned, was immersed in the above-described epoxysilane solution and left at room temperature for 20 hours. Thereafter, the glass substrate subjected to underlayer treatment was washed with ethanol, then washed with water, and dried. The average value of the water contact angle on the substrate surface after drying was 56°. Thus, a substrate treated with epoxysilane was obtained.

(Second Stage Reaction)

Polyethylene glycol (molecular weight 400) in an amount of 45 g was stirred, during which a catalytic amount of concentrated sulfuric acid was slowly added, and the resulting mixture was stirred at room temperature for several minutes. The above-described substrate treated with epoxysilane was immersed in the above-described polyethylene glycol so as to allow reaction to proceed at 120° C. for 30 minutes. After the reaction, the substrate was washed well with water and then dried. Accordingly, a glass substrate on which a hydrophilic thin film was formed could be prepared.

(Patterning Step)

A photomask of a 5-inch size having a pattern in which a plurality of circular openings of the same size were formed was used. The photomask had a patter in which circular openings each having a diameter of 1.5 mm were formed, and the space between two openings, that is to say, the shortest distance between each two openings was 0.35 mm.

The mask was gently placed on the film formation surface of the glass substrate on which a hydrophilic thin film was formed, the back side of the mask was irradiated with vacuum ultraviolet rays using a xenon excimer lamp (172 nm, 10 mW/cm$^2$) as a light source for 1 minute. Accordingly, areas corresponding to the openings of the photomask on the surface of the hydrophilic thin film were oxidized. The substrate was cut to 5-cm square pieces and used for cell culture.

The shape of each cell-adhesive region in the obtained cell culture substrate was circular, its diameter was 1.5 mm, and the space between two cell-adhesive regions, that is to say, the shortest distance between each two cell-adhesive regions was 0.35 mm. In addition, the proportion of cell-adhesive regions on a cell culture substrate was 51.8%.

2. Culture of Gut Organoids 2.1. Cell Lines

The human ES cell (hESC) lines SEES1, SEES2, and SEES3 generated in the Department of Cell Engineering, Department of Reproductive Biology of NCCHD were used (Akutsu H, et al. Regen. Ther. 2015;1:18-29). These ES cells were maintained on γ-ray-irradiated mouse embryonic fibroblast (MEF) feeder layers in a commercially available serum-free DMEM (trade name: KnockOut™ D-MEM (Thermo Fisher Scientific)) containing 20% KnockOut Serum Replacement (Life Technologies), 0.1 mM non-essential amino acids (NEAA), 1 mM pyruvic acid, 2 mM GlutaMAX-I, 0.055 mM β-mercaptoethanol, 50 U/ml penicillin/50 μg/ml streptomycin (Pen-Strep), and 8 ng/ml recombinant human bFGF (all purchased from Life Technologies). The medium was changed every two days. Cells were subcultured approximately once a week using enzymatic (dispase; Wako Pure Chemical Industries) or mechanical methods (EZPassage; Life Technologies).

Human iPS cells (hiPSCs) were generated in the Department of Cell Engineering, Department of Reproductive Biology of NCCHD by causing the human fetal lung-derived fibroblast cell line MRC5 to express four Yamanaka factors (Oct3/4, Sox2, Klf4, and c-Myc) using a retroviral vector (Makino H, et al. Exp Cell Res. 2009; 315 (16):2727-2740; Nishino K, et al. PLoS ONE. 2010; 5(9): e13017; Toyoda M, et al. Genes Cells. 2011; 16(1): 1-11). These human iPS cells were maintained on a y-ray-irradiated MEF feeder layers in iPSellon medium (Cardio Incorporated) supplemented with 10 ng/ml bFGF.

2.2. Generation of human gut organoids

In a previous study, the present inventors established xenogeneic-free (XenoFree, XF) conditions for generating and expanding human ES cells (Akutsu H, et al. Regen. Ther. 2015; 1: 18-29). Human ES cells were stably maintained in XF hESC medium containing 85% KnockOut™ D-MEM, 15% KnockOut™ Serum Replacement XF CTS (XF-KSR; Life Technologies), 1 mM pyruvic acid, 2 mM GlutaMAX-I, 0.1 mM NEAA, Pen-Strep, 50 μg/ml L-ascorbic acid 2-phosphate (Sigma-Aldrich), 10 ng/ml heregulin-1β (recombinant human NRG-β1/HRG-β1 EGF domain; R&D Systems), 200 ng/ml recombinant human IGF-1 (LONG R3-IGF-1; Sigma-Aldrich), and 20 ng/ml human bFGF (Life Technologies).

The following three types of media were prepared as differentiation induction media.

Regarding the medium composition, "%" refers to "% by volume" unless otherwise specified.

Differentiation induction medium 1 (sometimes herein referred to as "XF-KSR (−) medium"): Medium containing 80% KnockOut™ D-MEM, 20% KnockOut™ Serum Replacement XF CTS (XF-KSR; Life Technologies), 1 mM pyruvic acid, 2 mM GlutaMAX-I, 0.1 mM NEAA, Pen-Strep, 0.055 mM β-mercaptoethanol, and 10 μM Y-27632

Differentiation induction medium 2 (sometimes herein referred to as "XF hESC medium"): Medium containing 85% KnockOut™ D-MEM, 15% KnockOut™ Serum Replacement XF CTS (XF-KSR; Life Technologies), 1 mM pyruvic acid, 2 mM GlutaMAX-I, 0.1 mM NEAA, Pen-Strep, 50 μg/ml L-ascorbic acid 2-phosphate (Sigma-Aldrich), 10 ng/ml heregulin -1β (recombinant human NRG-β1/HRG-β1 EGF domain; R&D Systems), 200 ng/ml recombinant human IGF-1 (LONG R3-IGF-1; Sigma-Aldrich), and 20 ng/ml human bFGF (Life Technologies)

Differentiation induction medium 3 (sometimes herein referred to as "XF-KSR medium"): Medium containing 80% KnockOut™ D-MEM, 20% KnockOut™ Serum Replacement XF CTS (XF-KSR; Life Technologies), 1 mM pyruvic acid, 2 mM GlutaMAX-I, 0.1 mM NEAA, Pen-Strep, and 0.055 mM β-mercaptoethanol To generate gut organoids, undifferentiated hESCs or hiPSCs were dissociated using dispase and plated on a cell culture substrate prepared by the above-described protocol coated with 0.1% human recombinant type I collagen peptide (RCP) (Fujifilm) in 90-mm culture dishes. Other matrices such as vitronectin (Life Technologies) can also be used for this protocol. Matrix-coated dishes were prewarmed at 37° C. for 1 hour, the coating solution was removed, and the substrates were washed 3 times with PBS. The cells (4×10$^6$ cells in 3 ml of culture medium) were plated onto the substrate and maintained for 10 minutes. Thereafter, the medium was aspirated off, and 10 ml of fresh differentiation induction medium 1 was added gently. The differentiation induction medium 1 contains the Rho-associated protein kinase inhibitor Y-27632 (Wako Pure Chemical Industries) without growth factors as described above. hESCs or hiPSCs were cultured in the differentiation induction medium 1 containing Y-27632 without growth factors for 1 day and then in the differentiation induction medium 3 free of growth factors and Y-27632, which was replaced after 3 days with the differentiation induction medium 2 containing growth factors. Thereafter, the cells were cultured in the differentiation induction medium 2 while the medium was changed as appropriate. The differentiation induction medium 2 was gently changed every 3 to 4 days. After 40 days, a plurality of gut-like peristaltic organoids were collected and cultured together in 60-mm Ultralow Adhesion plates (NOF Corporation) in the differentiation induction medium 2. In addition, in another experiment, undifferentiated hESCs or hiPSCs were plated on the substrates by the same protocol and cultured in the differentiation induction medium 1 until day 4, and the same operation was carried out except that the medium was changed to the differentiation induction medium 2 on day 4.

Culture was carried out in an incubator at 37° C. and a $CO_2$ concentration of 5%, during which the cells were allowed to stand still, unless otherwise specified.

2.3. Video Recording of Human Gut Organoids

Floating organoids were picked, placed into culture plates with the differentiation induction medium 2, and analyzed by video recording using an inverted microscope equipped with a camera (Cohu 3600) of ZILOS-tk system (Hamilton Thorne). To count contracting gut organoids, all human embryonic stem cell (hiPSC)-derived floating organoids from one plate were collected in a new dish and recorded for 10 minutes. Peristalsis-like contracting organoids were counted as positive.

2.4. Quantitative RT-PCR Analysis

RNA was isolated from organoids using the RNeasy Mini Kit (Qiagen), and contaminating DNA was removed using DNase (Life Technologies). cDNA was synthesized using SuperScript III reverse transcriptase and an oligo-dT primer (Life Technologies) according to the manufacturer's instructions. Quantitative RT-PCR was performed in using the SYBR Green PCR Master mix and a QuantStudio 12K Flex Real-Time PCR System (Life Technologies) (n=3). Primer sequences are listed in the following table.

TABLE 1

| Gene | Forward primer (5'→3') (SEQ ID NO:) | Reverse primer (3'→5') (SEQ ID NO:) |
|---|---|---|
| ABCB1 | AAGGCCTAATGCCGAACACA (1) | GTCTGGCCCTTCTTCACCTC (2) |
| ABCG2 | TGTGGCATTAAACAGAGAAGAAGAC (3) | TCACCCCCGGAAAGTTGATG (4) |
| CD34 | AGAAAGGCTGGGCGAAGACCCT (5) | AGTGGGGAAGGGTTGGGCGT (6) |
| CDX2 | GGAACCTGTGCGAGTGGAT (7) | TCGATATTTGTCTTTCGTCCTG (8) |
| CKIT | TAAAGGTAACAACAAAGAGCAAATCC (9) | AGGTCAGAATCATCACAATAATGCA (10) |
| CXCR4 | GGGCAATGGATTGGTCATCCT (11) | TGCAGCCTGTACTTGTCCG (12) |
| ECAD | ATTTTTCCCTCGACACCCGAT (13) | TCCCAGGCGTAGACCAAGA (14) |
| FOXA2 | GGAGCAGCTACTATGCAGAGC (15) | CGTGTTCATGCCGTTCATCC (16) |
| GATA4 | GTGTCCCAGACGTTCTCAGTC (17) | GGGAGACGCATAGCCTTGT (18) |
| GATA6 | GTGCCAACTGTCACACCACA (19) | GAGTCCACAAGCATTGCACAC (20) |
| LCT | TGACCAATCCGAACACGGAG (21) | CAGAGACCAGGCGACATACC (22) |
| LGR5 | CACCTCCTACCTAGACCTCAGT (23) | CGCAAGACGTAACTCCTCCAG (24) |
| OCT4 | CGAGGAATTTGCCAAGCTCTGA (25) | TTCGGGCACTGCAGGAACAAATTC (26) |
| SLC15A1/PEPT1 | CACCTCCTTGAAGAAGATGGCA (27) | GGGAAGACTGGAAGAGTTTTATCG (28) |
| PGP9.5 | GTCCCCTGAAGACAGAGCAAA (29) | TTCACCGGAAAAGGCATTCG (30) |
| SMA | TGGCTTGGCTTGTCAGGGCTT (31) | CCCGGGGGCTGTTAGGACCTT (32) |
| SOX9 | AGCGAACGCACATCAAGAC (33) | CTGTAGGCGATCTGTTGGGG (34) |
| SOX17 | GTGGACCGCACGGAATTTG (35) | GGAGATTCACACCGGAGTCA (36) |
| VIL1 | CGGAAAGCACCCGTATGGAG (37) | CGTCCACCACGCCTACATAG (38) |
| Lysozyme | AAATACTGGGGCCAGCTCAC (39) | GCCCTGGACCGTAACAGAAA (40) |
| INS | CCAGCATCTGCTCCCTCTAC (41) | TGCTGGTTCAAGGGCTTTAT (42) |
| ALBUMIN | CGCTATTAGTTCGTTACACCA (43) | TTTACAACATTTGCTGCCCA (44) |
| T | TATGAGCCTCGAATCCACATAGT (45) | CCTCGTTCTGATAAGCAGTCAC (46) |
| SOX1 | ACCAGGCCATGGATGAAG (47) | CTTAATTGCTGGGGAATTGG (48) |
| GAPDH | CTCACCGGATGCACCAATGTT (49) | CGCGTTGCTCACAATGTTCAT (50) |

After amplification, dissociation curves were obtained to ensure that every PCR product was amplified. GAPDH was adopted as a reference housekeeping gene. QuantStudio 12K Flex software v1.0 was used to quantify the relative expression levels of mRNA of the target genes after normalization against the mRNA expression level of GAPDH. Healthy human adult small intestinal tissue (R1234226-50, BioChain Institute) and human adult pancreas and liver cDNAs (HA-188 and HA-149, respectively, Alpha Diagnostic International) were used as positive controls.

2.5. Immunocytochemistry

Organoids were fixed with 4% paraformaldehyde in PBS (Wako Pure Chemical Industries) for 5 minutes at 4° C., permeabilized with 0.2% Triton X-100 for 2 minutes at room temperature, and blocked with PBS containing 5% normal serum as appropriate for each antibody. The treated organoids were then incubated overnight at 4° C. with primary antibodies against the following antigens. The antigens are as follows: villin (sc-7672, 1:50, Santa Cruz Biotechnology); E-cadherin (610181, 1:50, BD Pharmingen); CGA (ab16007, 1:100), CDX2 (ab76541, 1:100), and PGP9.5 (ab8189, 1:10) (from Abcam); DEFA6 (HPA019462, 1:500) and SMA (A2547, 1:400) (from Sigma-Aldrich); MUC2 (sc-7314, 1:50, Santa Cruz Biotechnology); LGRS (LMC-1235, 1:100, Medical & Biological Laboratories); CKIT (NB100-77477AF488, 1:10, Immuno-Biological Laboratories); $Na^+/K^+$-ATPase (NB300-146, 1:100, Novus Biologicals); S-100 (422091, 1:100, Nichirei Biosciences); neurofilaments (M076229, 1:50, Dako); (3-actin (A5316, 1:1,000, Sigma-Aldrich); histamine H1 receptor (aa471-484, 1:200, LSBio); and CFTR (ab131553, 1:100, Abcam). Alexa 488- or Alexa 546-conjugated anti-mouse, anti-rabbit, or anti-goat secondary antibodies (BD Biosciences) were used. Cell nuclei were counterstained with DAPI. Cell fluorescence was analyzed using an LSM 510 Meta Laser Scanning Confocal Microscope (Carl Zeiss Microscopy).

2.6. Histochemical Analysis

Organoids were fixed in 4% paraformaldehyde, embedded in paraffin, and serially sectioned into 4-μ tm sections. Alternate sections were mounted on slides, stained with H&E, and analyzed. For Alcian Blue staining, sections were incubated in 1% Alcian Blue in 3% acetic acid, pH 2.5, for 20 minutes and in 0.1% nuclear Fast Red for 2 minutes, dehydrated in ethanol, and cleared using xylene.

Immunohistochemical analysis of organoids was carried out using sections stained with antibodies against SMA and serotonin (ab16007, 1:20, Abcam). The secondary antibody used herein was polyclonal rabbit anti-mouse immunoglobulin-HRP (1:100; Dako).

2.7. Electron Microscopic Observation

Gut organoid samples for electron microscopic observation were prepared according to a standard protocol (Tokai Electron Microscopy). Briefly, organoids were fixed with 2% paraformaldehyde and 2% glutaraldehyde in PBS, dehydrated, and embedded in the epoxy resin. After polymerization, the samples were sectioned at 70 nm, mounted on copper grids, and observed under a JEM-1200EX TEM (Jeol Ltd.) equipped with a Veleta CCD camera (Olympus).

2.8. Cell Transfection

To monitor differentiation status during gut organogenesis, the present inventors generated an intestinal lineage-specific reporter construct (pPB-hLgr5p-EGFP-neo). pPB-hLgr5p-EGFP-neo contains the 5-kb LGRS promoter and the phosphoglycerine kinase (PGK) promoter to drive expression of EGFP and the neomycin resistance gene (neo), respectively. SEES1 cells were cultured with Y-27632 for 24 hours prior to electroporation, washed with PBS, harvested using Accutase solution (Life Technologies), and resuspended in iPSellon medium. Cells were dissociated into a single-cell suspension by vigorous pipetting; 1 to $2\times10^6$ cells were pelleted and mixed with the pPB-hLgr5p-EGFP-neo reporter vector and the hyperactive PiggyBac transposase expression vector (pCMV-hyPBase) (a gift from A. Bradley, Wellcome Trust Sanger Institute, Hinxton, Cambridge, United Kingdom) in Opti-MEM (Life Technologies). The obtained cell suspension was transferred to a cuvette and electroporated using the NEPA21 Super Electroporator (Nepa Gene), thereby obtaining transfected cells. Transfected cells were selected with G418 (Sigma-Aldrich).

To visualize the in vivo performance of transplanted gut organoids, human embryonic stem cells (hESC) cells were transfected with the constitutive EGFP expression vector (pmGENIE-EGFP) (a gift from S. Moisyadi, University of Hawaii, Honolulu, Hawaii, USA). After screening, a stable GFP-positive positive human embryonic stem cell (hESC) line was established.

2.9. Evaluation of In Vitro β-Ala-Lys-AMCA Uptake by Human Gut Organoids

Gut organoids grown in the differentiation induction medium 2 were washed with PBS and cultured in DMEM containing 25 μM fluorophore-conjugated dipeptide β-Ala-Lys-AMCA (Biotrend Chemicals) for 4 hours at 37° C. For inhibition experiments, gut organoids were cultured with or without 1 mM of angiotensin-converting enzyme inhibitor captopril (Sigma-Aldrich) for 1 hour, rinsed with PBS, placed into the same dish, and observed under a fluorescence microscope (Olympus). In addition, to quantify the uptake of β-Ala-Lys-AMCA, gut organoids were cultured with or without 10 μM, 100 μM, or 1 mM of captopril, and AMCA-related signals were observed using a fluorescence microscope (BZ-X710; Keyence) equipped with a top-stage incubator (5% CO2 at 37° C.), and the fluorescence signal intensity was quantified using the Hybrid Cell Count/BZ-H3C (Keyence). All sample images were recorded under standard conditions. For each concentration, 3 independent assays were performed.

2.10. In Vitro Contractility of Human Gut Organoids

A single human embryonic stem cell (hESC)-derived gut organoid showing peristalsis-like movement (days 80-90 in culture) was treated with the peristaltic stimulator histamine (0.2 μM) and the cholinergic antagonist atropine sulfate (0.2 μM). Contractility responses were recorded using an inverted microscope. Image analysis software CL-Quant version 3.10 (Nikon Corporation) was used to visualize movements in the gut organoid. First, in each frame of the time-lapse images, the software was used to identify a specific region of the organoid. Second, the software fitted an ellipse to this region and calculated the ratio of the longest to shortest diameter to obtain an aspect ratio. Changes in the aspect ratios with time were plotted on the chart. Videos were recorded at 30 frames per second.

2.11. CFTR Transport Activity of Gut Organoids

Each organoid was placed into a well of an ART culture dish 12 (NIPRO) containing 100 μl culture medium. Organoids derived from EGFP-human embryonic stem cells (hESCs), which constitutively express EGFP under the CMV promoter, were used to visualize volume changes. Five μM forskolin was added, and organoid morphology was monitored by time-lapse fluorescence laser confocal microscopy (Keyence). To inhibit CFTR, organoids were preincubated with 50 μM of the CFTR inhibitor CFTRinh172 and 50 μM GlyH-101 (TOCRIS) for 3 hours. Images were collected every minute for 20 minutes in a top-stage incubator (5% $CO_2$ at 37° C.). Each experimental treatment was assessed in triplicate wells. DMSO concentration was identical under all conditions and did not exceed 0.2% (w/v). The organoid surface area was quantified using Hybrid Cell Count/BZ-H3C (Keyence). The normalized total organoid surface area was calculated and averaged from 3 individual wells per experimental condition.

2.12. Transplantation of Human Gut Organoids

The in vivo development of gut organoids was assessed by transplantation into immunodeficient nude mice (BALB/cAJcl-nu/nu) purchased from CLEA Japan. A single day 35 gut organoid was transplanted below the kidney capsule of each mouse. The transplanted mice were humanely euthanized by cervical dislocation after 6 weeks, and the kidneys were examined under an MVX10 fluorescence microscope (Olympus). The transplanted site was further analyzed by H&E staining and immunocytochemistry.

2.13. Statistics

Quantitative data are reported as mean±SEM from at least 3 independent experiments. Statistical analysis was performed using either an unpaired, 2-tailed t test or a Mann-Whitney rank-sum test. P<0.05 was considered to indicate a statistically significant difference.

3. Results

FIG. 1A to FIG. 9B depict the representative results.

FIG. 1A to FIG. 1D explain the generation of motile gut organoids from human pluripotent stem cells on a cell culture substrate on which cell-adhesive regions are patterned.

FIG. 2A to FIG. 2D explain characteristics of gut organoid differentiation.

FIG. 3A to FIG. 3C depict the characteristics of gut organoids and results of detection of GR5-EGFP-positive cells in the process of gut organoid generation.

FIG. 4A to FIG. 4F explain the contractile activity of gut organoids.

FIG. 5A to FIG. 5C explain the absorption function of gut organoids.

FIG. 6A and FIG. 6B explain the CFTR transport activity of gut organoids.

FIG. 7A to FIG. 7D show characteristics of nonmotile gut organoids.

FIG. 8A to FIG. 8D indicate that once gut organoids (on day 35 in culture) are transplanted, an advanced intestine tract structure can be formed.

FIG. 9A and FIG. 9B indicate changes in the process of culture of human iPS cell-derived gut organoids.

Experimental results will be described below with reference to the drawings as appropriate. A specific description of the drawings is given in the section of "Brief Description of Drawings."

3.1. Gut Organoids Self-Organize on a Cell Culture Substrate on Which Cell-Adhesive Regions are Patterned In general, tissue self-organization has three major steps: self-assembly, self-patterning, and self-morphogenesis (Sasai Y. Nature. 2013;493(7432):318-326). In this experiment, by applying this three-step concept, gut morphogenesis via a cellular patterning-bulging phase and a self-morphogenesis phase is induced (FIG. 1A). In the first step, human embryonic stem cells (hESCs) or human iPS cells (hiPSCs) that had been cultured in XF medium (Akutsu H, et al. Regen. Ther. 2015;1:18-29) were assembled on circular-patterned cell-adhesive regions on the glass surface of a cell culture substrate (Okochi N, Okazaki T, Hattori H. Langmuir. 2009; 25 (12): 6947-6953) in differentiation induction medium 2. The cells accumulated in the cell-adhesive regions and formed hemispheric dome-like structures after 7 days in culture (FIG. 1C). Subsequently, enlarged cavitated structures formed. These structures exhibited epithelial folding and cyst-like protrusions of a self-organized cell mass and, by day 20 in culture, were lined with cuboidal epithelial cells. By day 30 in culture, self-organized cystic spheroids began to detach from the cell culture substrate. These detached spheroids mostly belonged to two morphological types. One type of cells were spheroids having simple cystic forms with thin cellular walls. Another type of cells were bi-component spheroids with solid and partially cystic protrusions. Remarkably, the bi-component spheroids exhibited contractile movements. These spheroids comprised 4% (32 of 791, n=3) of all detached organoids, and they were maintained over an extended period (see FIG. 1D). This suggests that the organoids consisted of cell types that originated from different germ layers and that were assembled into a functional cellular network.

Next, the present inventors examined expression of germ layer markers at different differentiation time points. In the early differentiation phase, growing patterned cells expressed markers of definitive endoderm, namely, FOXA2, SOX17, and CXCR4, and of early endoderm and mesoderm, namely, GATA4, GATA6, and T (Brachyury) (FIG. 2A). The expression levels of these markers increased during formation of the hemispheric dome-like structures until day 14 in culture (FIG. 1A and FIG. 2A). As differentiation further progressed, the level of CXCR4 expression fell on day 21 in culture. This finding was consistent with the reported down-regulation of gene expression during hindgut formation in mouse embryo development (McGrath K E, Koniski A D, Maltby K M, McGann J K, Palis J. Dev Biol. 1999; 213 (2): 442-456). The level of the hindgut marker CDX2 increased during early growth and was maintained at a relatively high level as differentiation progressed (FIG. 2A). The expression of the neural progenitor marker SOX1 increased at a relatively late stage (day 21) compared with other germ layer markers (FIG. 2A). By contrast, the expression level of pluripotent cell marker OCT4 showed a significant decrease during early differentiation. Thus, the present inventors' protocol promoted human ES cell differentiation into definitive endoderm and hindgut by day 21 in culture, with the formation of hemispheric dome-like structures.

During subsequent differentiation, cell accumulations formed cavitated structures and detached from the cell culture substrate (FIG. 1C). The epithelium of each structure exhibited multiple folds. H&E staining of paraffin-embedded organoids that exhibited contractile movements showed that the gut architecture consisted of mucosa and submucosa (FIG. 2B). The intestinal mucosa is formed by the epithelium and lamina propria. The intestinal epithelium consists of two cell types, absorptive enterocytes and secretory lineage cells, including mucus-producing goblet cells, enteroendocrine cells, and Paneth cells (Gracz A D, Magness S T. Am J Physiol Gastrointest Liver Physiol. 014; 307 (3): G260-G273). Alcian Blue staining showed the presence of purple-stained mucopolysaccharide-containing goblet cells in the epithelium of the organoids (FIG. 2C). Interestingly, the relative expression of some late differentiation gene markers in mature organoids on day 50 in culture was similar to that of a human adult intestine (FIG. 2D). As intestinal epithelial cells matured, CDX2 (an intestinal transcription factor), ECAD (an epithelial cell—specific E-cadherin), and a brush border-specific villin expressed in gut organoids at the same level as in the human adult intestine.

As a result of immunostaining, it was confirmed that villin localized to the apical surface of the epithelium and that CDX2 was present in the epithelial layer (FIG. 3A). The image of the organoids observed by transmission electron microscopy (TEM) confirmed the occurrence of a brush border in the apical microvilli (FIG. 3B). Paneth cells were identified by staining for the Paneth cell—specific defensin α-6 (DEFA6) (FIG. 3A), and were confirmed to contain secretory granules by TEM (FIG. 3B) H&E and Alcian Blue staining identified resident goblet cells in the epithelial layers. Their identity was confirmed by mucin-2 (MUC2) staining (FIG. 3A) and by the presence of mucin granules in the TEM observation image (FIG. 3B). The expression level of chromogranin A (CGA), an epithelial enteroendocrine cell marker, was lower in gut organoids than in the human adult intestine (FIG. 2D); however, immunostaining for ECAD and CGA showed the presence of both proteins in the epithelium (FIG. 3A). The intestinal stem cell marker LGR5 was coexpressed with CDX2 in gut organoids (FIG. 3A). LGR5 expression was also confirmed during gut organogenesis in human embryonic stem cells (hESCs) transfected with the EGFP expression vector under the LGR5 promoter regulation (FIG. 3C). Thus, self-organized gut organoids according to an embodiment of the present invention exhibited diverse types of highly differentiated intestinal cells.

3.2. Gut Organoids Show Functional Features Particular to Mature Gut.

The gut organoids were analyzed for intestinal-specific functions, namely contractile activity, peptide absorption, and fluid secretion. Gut organoids showed contractile movements, indicating the presence of a functionally mature mesenchymal layer. Gut motility is controlled by the enteric nervous system and pacemaker cells such as interstitial cells of Cajal (ICC) (Sanders K M, Koh S D, Ward S M. Annu Rev Physiol. 2006; 68: 307-343; uizinga J D, Lammers W J. Am J Physiol Gastrointest Liver Physiol. 2009; 296 (1): G1-G8). To determine which cell types were responsible for the contractile movements of the intestine, an immunochemical analysis was performed. Mesoderm-derived smooth muscle cells were identified in the submucosal area by staining for α-smooth muscle actin (SMA) (FIG. 4A). This indicated the contribution of mesoderm to the formation of organoids. Intestinal subepithelial myofibroblasts support in vitro and in vivo growth of human intestinal epithelium (Lahar N, et al. PLoS One. 2011; 6 (11): e26898). Quantitative RT-PCR was used to identify cells showing expression of protein gene product 9.5 (PGP9.5), a neural marker for the enteric nervous system (FIG. 3A), and the ICC markers CD34 and CKIT (FIG. 2D). In addition, immunostaining was used to identify cells doubly positive for CKIT and S-100, a glial cell marker; these cells were localized in submucosal regions (FIG. 4B). Serotonin is a major neurotransmitter that regulates gastrointestinal functions (such as peristalsis and secretion); it is synthesized by enteroendocrine cells of the intestinal mucosa (Mawe G M, Hoffman J M. Nat Rev Gastroenterol Hepatol. 2013;10 (8): 473-486). Immunohistochemical analysis revealed that serotonin-positive cells were present in the epithelial layers of gut organoids (FIG. 4C). Histamine treatment increased the rate of gut organoid contractile activity, whereas atropine treatment decreased the rate (FIG. 4D). The modulation of contractile activity after treatment with histamine or atropine confirmed that the gut organoids showed similar motility as mature intestine (Mittal R K, Padda B, Bhalla V, Bhargava V, Liu J. Am J Physiol Gastrointest Liver Physiol. 2006; 290(3): G431-G438). As described above, motile gut organoids also responded to the drugs; however, nonmotile organoids were never observed to respond to the contractile activator histamine (n=6, FIG. 4E). By contrast, histamine H1 receptors were expressed in epithelial and mesenchymal regions in motile organoids and human intestines (FIG. 4F). Nonmotile gut organoids also expressed the histamine H1 receptor and were confirmed to be gut-like tissue by quantitative RT-PCR and immunostaining analyses for intestine tissue-specific genes (FIG. 7A). The markers of mature endoderm derivatives, ALBUMIN and INSULIN, were not expressed in gut organoids (FIG. 7B). Nonmotile organoids showed similar levels of expression of the genes as adult intestine; however, immunostaining analysis showed that the nonmotile organoids displayed immaturity/disorganization of the mesenchymal layers. The smooth muscle cell marker SMA in nonmotile gut organoids showed a low level of staining compared with motile organoids (FIG. 7C). Neurofilaments were distributed throughout the mesenchymal area of motile organoids but were present much more infrequently in nonmotile organoids (FIG. 7D). Immaturity of muscle cell layers and neurons in the mesenchymal area might be the cause of nonmotility in these organoids.

To examine peptide absorption in gut organoids, the expression levels of intestinal oligopeptide transporter (PEPT1) and the major ATP-binding cassette (ABC) transporters, ABCB1 and ABCG2, were screened. Levels of expression of these genes in gut organoids were similar to those in the adult intestine (FIG. 5A). Active peptide transport was evaluated in an ex vivo assay (Groneberg D A, Doring F, Eynott P R, Fischer A, Daniel H. Am J Physiol Gastrointest Liver Physiol. 2001; 281(3): G697-G704). Gut organoids cultured with the fluorophore-conjugated dipeptide β-Ala-Lys-N(c)-7-amino-4-methylcoumarin-3-acetic acid showed peptide absorption, which decreased after treatment with captopril (FIG. 5B). There was no indication of captopril dose dependency due to the peptide absorption blocking action after treatment with different concentrations of captopril (FIG. 5C).

In order to examine secretory activity of organoids, the present inventors checked the expression level of the cystic fibrosis conductance regulator (CFTR) and also performed a forskolin-induced swelling (FIS) assay. CFTR is critical to fluid secretion in intestinal epithelial cells. The present inventors confirmed the presence of CFTR in epithelial layers of the gut organoids, as well as in the human intestine (FIG. 6A). To demonstrate CFTR function, the present inventors used the FIS assay used in the art (Dekkers J F, et al. Nat Med. 2013;19(7):939-945) and found that gut organoids were swollen by forskolin induction. In addition, CFTR blockers completely inhibited this swelling (FIG. 6B). Based on these results, the present inventors concluded that the gut organoids displayed absorptive and secretory activities similar to those of mature intestine.

These experimental results indicate that stem cell-derived gut organoids produced in xenogeneic-free conditions have a well-organized structure containing major intestinal cell lineages and show intestinal functions similar to those of mature intestine. A previous study showed that maturation and differentiation occurred in gut organoids transplanted under mouse kidney capsules (Watson C L, et al. Nat Med. 2014; 20 (11): 1310-1314). To confirm the maturity of the gut organoids derived in vitro from stem cells, single day 35 organoids derived from human embryonic stem cells (hESCs) and constitutively expressing EGFP under CMV promoter regulation were transplanted under the renal capsules of immunodeficient nude mice (FIG. 8A). All transplanted organoids (n=4) successfully engrafted and displayed highly structured intestinal tract morphology, with a lumen and laminated layers (FIGS. 8B and 8C). The present inventors also observed expression of the intestinal epithelial and mesenchymal gene markers CDX2 (enterocytes), MUC2 (goblet cells), CGA (enteroendocrine cells), DEFA6 (Paneth cells), and ECAD and $Na^+/K^+$-ATPase (epithelium) as well as the enteric neuronal marker PGP9.5 in the layered SMA-positive mesenchyme (FIG. 8D). Thus, all intestinal cell types were present in the transplanted gut organoids. Transplantation experiments showed that gut organoids did not grow much after transplantation, indicating that they were highly differentiated in vitro.

4. Discussion

The above results demonstrate that human stem cell-derived gut organoids produced in xenogeneic-free conditions have a well-organized structure and contain the major intestinal cell lineages. These organoids display similar functional characteristics to mature intestine. The gut organoid obtained in this experiment has at least three advantages.

First, gut organoids can be maintained for long-term periods under xenogeneic-free conditions and suitable for clinical applications in regenerative medicine.

Second, gut organoids have a complex tissue architecture and show similar functions as mature intestines. Unlike epithelium-derived epithelial organoids, gut organoids contain both intestinal epithelium and mesenchymal layers. Gut organoids show the epithelial functions of peptide absorption and fluid secretion and display peristalsis-like movements in response to histamine and atropine similar to those of mature human intestine. This suggests that gut organoids can be used as "miniature guts." The gut organoid system may be highly valuable for investigations into gut-associated diseases.

Third, this is the first example showing that functional organoids containing all 3 germ layers, endoderm, mesoderm, and ectoderm, can be generated from stem cells in vitro.

INDUSTRIAL APPLICABILITY

The gut organoid provided by an embodiment of the present invention is useful for investigation of mechanisms of intestinal diseases and development of therapeutic drugs.

According to the method for producing a gut organoid provided by an embodiment of the present invention, gut organoids can be readily produced in vitro for studies on diseases and drug development.

All publications, patents and patent applications cited in the present description are incorporated herein by reference in their entirety.

---

The invention claimed is:

1. An in vitro gut organoid comprising:
   a tissue structure that encloses a cavity, wherein:
   the cavity is a closed cavity that is able to hold liquid;
   the tissue structure comprises endodermal cells, mesodermal cells, and ectodermal cells; and
   the endodermal cells comprise intestinal epithelial cells that are at least part of the outermost surface of the tissue structure.

2. The in vitro gut organoid according to claim 1, wherein the intestinal epithelial cells comprise transporter-positive intestinal epithelial cells.

3. The in vitro gut organoid according to claim 1, wherein the endodermal cells, mesodermal cells, and ectodermal cells are derived from at least one of embryonic stem cells or induced pluripotent stem cells.

4. The in vitro gut organoid according to claim 1, wherein the endodermal cells, mesodermal cells, and ectodermal cells are only derived from at least one of embryonic stem cells or induced pluripotent stem cells.

5. The in vitro gut organoid according to claim 1, wherein the in vitro gut organoid has a longitudinal length of 5 mm or more.

6. The in vitro gut organoid according to claim 1, wherein the tissue structure comprises intestinal epithelium and mesenchymal layers.

7. The in vitro gut organoid according to claim 1, wherein the in vitro gut organoid is able to secrete mucus, absorb a peptide, and perform contractile movement.

8. The in vitro gut organoid according to claim 1, wherein the in vitro gut organoid is able to secrete mucus out of the gut organoid.

9. The in vitro gut organoid according to claim 1, wherein the intestinal epithelial cells comprise at least one of enterocytes, goblet cells, enteroendocrine cells, or Paneth cells.

10. The in vitro gut organoid according to claim 1, wherein the intestinal epithelial cells comprise enteroendocrine cells that are able to secrete serotonin.

11. The in vitro gut organoid according to claim 1, wherein the intestinal epithelial cells comprise cystic fibrosis conductance regulator (CFTR)-positive intestinal epithelial cells.

12. The in vitro gut organoid according to claim 1, wherein a substance from outside of the in vitro gut organoid is able to be absorbed into the cavity via the intestinal epithelial cells on the outermost surface of the tissue structure.

13. The in vitro gut organoid according to claim 1, wherein the intestinal epithelial cells comprise transporter-positive intestinal epithelial cells that have an intestine oligopeptide transporter (PEPT1).

14. The in vitro gut organoid according to claim 1, wherein the intestinal epithelial cells comprise transporter-positive intestinal epithelial cells that have an ATP-binding cassette (ABC) transporter.

15. The in vitro gut organoid according to claim 14, wherein the ABC transporter is an ABCB1 transporter or ABCG2 transporter.

16. The in vitro gut organoid according to claim 1, wherein the in vitro gut organoid is able to perform contractile movement.

17. The in vitro gut organoid according to claim 16, wherein frequency of contraction is increased by histamine treatment and decreased by atropine treatment.

18. The in vitro gut organoid according to claim 1, wherein the tissue structure comprises at least one of intestinal nerve cells, smooth muscle cells, or interstitial cells of Cajal.

19. The in vitro gut organoid according to claim 18, wherein the intestinal epithelial cells comprise at least one of enterocytes, goblet cells, enteroendocrine cells, or Paneth cells.

20. The in vitro gut organoid according to claim 1, wherein the tissue structure further comprises intestine stem cells.

21. The in vitro gut organoid according to claim 1, wherein the tissue structure comprises microvilli on the outermost surface of the tissue structure.

22. The in vitro gut organoid according to claim 1, wherein the tissue structure comprises intestinal epithelium crypts.

23. An in vitro gut organoid comprising:
   a tissue structure that encloses a cavity, wherein:
   the cavity is a closed cavity that is able to hold liquid;
   the outermost surface of the tissue structure comprises an intestinal epithelium; and
   the tissue structure further comprises at least one of intestinal nerve cells, smooth muscle cells, or interstitial cells of Cajal.

24. An in vitro gut organoid comprising:
   a tissue structure that encloses a cavity, wherein:
   the cavity is a closed cavity that is able to hold liquid;
   the outermost surface of the tissue structure comprises villin; and
   the tissue structure further comprises at least one of intestinal nerve cells, smooth muscle cells, or interstitial cells of Cajal.

25. A method of using the in vitro gut organoid according to claim 1, comprising:
   providing a test drug to the in vitro gut organoid in the presence of a buffer solution so that liquid comprising the test drug enters into the cavity; and
   collecting and analyzing the liquid in the cavity.

26. The method according to claim 25, wherein the intestinal epithelial cells comprise transporter-positive intestinal epithelial cells.

27. The method according to claim 25, wherein the in vitro gut organoid performs contractile movement.

28. The method according to claim 25, wherein the in vitro gut organoid is able to perform contractile movement and frequency of contraction is increased by histamine treatment and deceased by atropine treatment.

29. The method according to claim 25, wherein the tissue structure comprises microvilli on the outermost surface of the tissue structure.

30. The method according to claim 25, wherein the tissue structure comprises intestinal epithelium crypts.

31. A method for producing the in vitro gut organoid according to claim 1, comprising:
- plating cells on a cell culture substrate that comprises a surface on which a cell-adhesive region and a non-cell-adhesive region surrounding the cell-adhesive region are formed; and
- culturing the cells plated on the cell culture substrate so as to induce differentiation of the cells into the endodermal cells, mesodermal cells, and ectodermal cells of the tissue structure.

32. The in vitro gut organoid according to claim 1, wherein an inner surface of the tissue structure comprises at least one of the mesodermal cells or ectodermal cells.

* * * * *

SEQUENCE LISTING

```
<160> NUMBER OF SEQ ID NOS: 50

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
aaggcctaat gccgaacaca                                               20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
ctccacttct tcccggtctg                                               20

<210> SEQ ID NO 3
<211> LENGTH: 25
<212> TYPE: DNA
<213> ORGANISM: Artificial Sequence
<220> FEATURE:
<223> OTHER INFORMATION: primer

<400> SEQUENCE: 3
tgtggcatta aacagagaag aagac                                         25

<210> SEQ ID NO 4
<211> LENGTH: 20
<212> TYPE: DNA
<213> ORGANISM: Artificial Sequence
```

```
<220> FEATURE:
<223> OTHER INFORMATION: primer

<400> SEQUENCE: 4
gtagttgaaa ggcccccact                                                     20

<210> SEQ ID NO 5
<211> LENGTH: 22
<212> TYPE: DNA
<213> ORGANISM: Artificial Sequence
<220> FEATURE:
<223> OTHER INFORMATION: primer

<400> SEQUENCE: 5
agaaaggctg ggcgaagacc ct                                                  22

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
tgcgggttgg gaaggggtga                                                     20

<210> SEQ ID NO 7
<211> LENGTH: 19
<212> TYPE: DNA
<213> ORGANISM: Artificial Sequence
<220> FEATURE:
<223> OTHER INFORMATION: primer

<400> SEQUENCE: 7
ggaacctgtg cgagtggat                                                      19

<210> SEQ ID NO 8
<211> LENGTH: 22
<212> TYPE: DNA
<213> ORGANISM: Artificial Sequence
<220> FEATURE:
<223> OTHER INFORMATION: primer

<400> SEQUENCE: 8
gtcctgcttt ctgtttatag ct                                                  22

<210> SEQ ID NO 9
<211> LENGTH: 26
<212> TYPE: DNA
<213> ORGANISM: Artificial Sequence
<220> FEATURE:
<223> OTHER INFORMATION: primer

<400> SEQUENCE: 9
taaaggtaac aacaaagagc aaatcc                                              26

<210> SEQ ID NO 10
<211> LENGTH: 25
<212> TYPE: DNA
<213> ORGANISM: Artificial Sequence
<220> FEATURE:
<223> OTHER INFORMATION: primer

<400> SEQUENCE: 10
acgtaataac actactaaga ctgga                                               25
```

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
gggcaatgga ttggtcatcc t                                              21

<210> SEQ ID NO 12
<211> LENGTH: 19
<212> TYPE: DNA
<213> ORGANISM: Artificial Sequence
<220> FEATURE:
<223> OTHER INFORMATION: primer

<400> SEQUENCE: 12
gcctgttcat gtccgacgt                                                 19

<210> SEQ ID NO 13
<211> LENGTH: 21
<212> TYPE: DNA
<213> ORGANISM: Artificial Sequence
<220> FEATURE:
<223> OTHER INFORMATION: primer

<400> SEQUENCE: 13
atttttccct cgacacccga t                                              21

<210> SEQ ID NO 14
<211> LENGTH: 19
<212> TYPE: DNA
<213> ORGANISM: Artificial Sequence
<220> FEATURE:
<223> OTHER INFORMATION: primer

<400> SEQUENCE: 14
agaaccagat gcggaccct                                                 19

<210> SEQ ID NO 15
<211> LENGTH: 21
<212> TYPE: DNA
<213> ORGANISM: Artificial Sequence
<220> FEATURE:
<223> OTHER INFORMATION: primer

<400> SEQUENCE: 15
ggagcagcta ctatgcagag c                                              21

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
cctacttgcc gtacttgtgc                                                20

<210> SEQ ID NO 17
<211> LENGTH: 21
<212> TYPE: DNA
<213> ORGANISM: Artificial Sequence
<220> FEATURE:
<223> OTHER INFORMATION: primer

<400> SEQUENCE: 17
gtgtcccaga cgttctcagt c                                                    21

<210> SEQ ID NO 18
<211> LENGTH: 19
<212> TYPE: DNA
<213> ORGANISM: Artificial Sequence
<220> FEATURE:
<223> OTHER INFORMATION: primer

<400> SEQUENCE: 18
tgttccgata cgcagaggg                                                       19

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
gtgccaactg tcacaccaca                                                      20

<210> SEQ ID NO 20
<211> LENGTH: 21
<212> TYPE: DNA
<213> ORGANISM: Artificial Sequence
<220> FEATURE:
<223> OTHER INFORMATION: primer

<400> SEQUENCE: 20
cacacgttac gaacacctga g                                                    21

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
tgaccaatcc gaacacggag                                                      20

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
ccatacagcg gaccagagac                                                      20

<210> SEQ ID NO 23
<211> LENGTH: 22
<212> TYPE: DNA
<213> ORGANISM: Artificial Sequence
<220> FEATURE:
<223> OTHER INFORMATION: primer

<400> SEQUENCE: 23
cacctcctac ctagacctca gt                                                   22

<210> SEQ ID NO 24

<210> SEQ ID NO 24
<211> LENGTH: 21
<212> TYPE: DNA
<213> ORGANISM: Artificial Sequence
<220> FEATURE:
<223> OTHER INFORMATION: primer

<400> SEQUENCE: 24
gacctcctca atgcagaacg c                                             21

<210> SEQ ID NO 25
<211> LENGTH: 22
<212> TYPE: DNA
<213> ORGANISM: Artificial Sequence
<220> FEATURE:
<223> OTHER INFORMATION: primer

<400> SEQUENCE: 25
cgaggaattt gccaagctct ga                                            22

<210> SEQ ID NO 26
<211> LENGTH: 24
<212> TYPE: DNA
<213> ORGANISM: Artificial Sequence
<220> FEATURE:
<223> OTHER INFORMATION: primer

<400> SEQUENCE: 26
cttaaacaag gacgtcacgg gctt                                          24

<210> SEQ ID NO 27
<211> LENGTH: 22
<212> TYPE: DNA
<213> ORGANISM: Artificial Sequence
<220> FEATURE:
<223> OTHER INFORMATION: primer

<400> SEQUENCE: 27
cacctccttg aagaagatgg ca                                            22

<210> SEQ ID NO 28
<211> LENGTH: 24
<212> TYPE: DNA
<213> ORGANISM: Artificial Sequence
<220> FEATURE:
<223> OTHER INFORMATION: primer

<400> SEQUENCE: 28
gctattttga gaaggtcaga aggg                                          24

<210> SEQ ID NO 29
<211> LENGTH: 21
<212> TYPE: DNA
<213> ORGANISM: Artificial Sequence
<220> FEATURE:
<223> OTHER INFORMATION: primer

<400> SEQUENCE: 29
gtcccctgaa gacagagcaa a                                             21

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
gcttacggaa aaggccactt                                              20

<210> SEQ ID NO 31
<211> LENGTH: 21
<212> TYPE: DNA
<213> ORGANISM: Artificial Sequence
<220> FEATURE:
<223> OTHER INFORMATION: primer

<400> SEQUENCE: 31
tggcttggct tgtcagggct t                                            21

<210> SEQ ID NO 32
<211> LENGTH: 21
<212> TYPE: DNA
<213> ORGANISM: Artificial Sequence
<220> FEATURE:
<223> OTHER INFORMATION: primer

<400> SEQUENCE: 32
ttccaggatt gtcgggggcc c                                            21

<210> SEQ ID NO 33
<211> LENGTH: 19
<212> TYPE: DNA
<213> ORGANISM: Artificial Sequence
<220> FEATURE:
<223> OTHER INFORMATION: primer

<400> SEQUENCE: 33
agcgaacgca catcaagac                                               19

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
ggggttgtct agcggatgtc                                              20

<210> SEQ ID NO 35
<211> LENGTH: 19
<212> TYPE: DNA
<213> ORGANISM: Artificial Sequence
<220> FEATURE:
<223> OTHER INFORMATION: primer

<400> SEQUENCE: 35
gtggaccgca cggaatttg                                               19

<210> SEQ ID NO 36
<211> LENGTH: 20
<212> TYPE: DNA
<213> ORGANISM: Artificial Sequence
<220> FEATURE:
<223> OTHER INFORMATION: primer

<400> SEQUENCE: 36
actgaggcca cacttagagg                                              20

<210> SEQ ID NO 37
<211> LENGTH: 20
<212> TYPE: DNA

<213> ORGANISM: Artificial Sequence
<220> FEATURE:
<223> OTHER INFORMATION: primer

<400> SEQUENCE: 37
cggaaagcac ccgtatggag        20

<210> SEQ ID NO 38
<211> LENGTH: 20
<212> TYPE: DNA
<213> ORGANISM: Artificial Sequence
<220> FEATURE:
<223> OTHER INFORMATION: primer

<400> SEQUENCE: 38
gatacatccg caccacctgc        20

<210> SEQ ID NO 39
<211> LENGTH: 20
<212> TYPE: DNA
<213> ORGANISM: Artificial Sequence
<220> FEATURE:
<223> OTHER INFORMATION: primer

<400> SEQUENCE: 39
aaatactggg gccagctcac        20

<210> SEQ ID NO 40
<211> LENGTH: 20
<212> TYPE: DNA
<213> ORGANISM: Artificial Sequence
<220> FEATURE:
<223> OTHER INFORMATION: primer

<400> SEQUENCE: 40
aaagacaatg ccaggtcccg        20

<210> SEQ ID NO 41
<211> LENGTH: 20
<212> TYPE: DNA
<213> ORGANISM: Artificial Sequence
<220> FEATURE:
<223> OTHER INFORMATION: primer

<400> SEQUENCE: 41
ccagcatctg ctccctctac        20

<210> SEQ ID NO 42
<211> LENGTH: 20
<212> TYPE: DNA
<213> ORGANISM: Artificial Sequence
<220> FEATURE:
<223> OTHER INFORMATION: primer

<400> SEQUENCE: 42
tatttcggga acttggtcgt        20

<210> SEQ ID NO 43
<211> LENGTH: 21
<212> TYPE: DNA
<213> ORGANISM: Artificial Sequence
<220> FEATURE:
<223> OTHER INFORMATION: primer

<400> SEQUENCE: 43
cgctattagt tcgttacacc a        21

<210> SEQ ID NO 44
<211> LENGTH: 20
<212> TYPE: DNA
<213> ORGANISM: Artificial Sequence
<220> FEATURE:
<223> OTHER INFORMATION: primer

<400> SEQUENCE: 44
acccgtcgtt tacaacattt                                                     20

<210> SEQ ID NO 45
<211> LENGTH: 23
<212> TYPE: DNA
<213> ORGANISM: Artificial Sequence
<220> FEATURE:
<223> OTHER INFORMATION: primer

<400> SEQUENCE: 45
tatgagcctc gaatccacat agt                                                 23

<210> SEQ ID NO 46
<211> LENGTH: 22
<212> TYPE: DNA
<213> ORGANISM: Artificial Sequence
<220> FEATURE:
<223> OTHER INFORMATION: primer

<400> SEQUENCE: 46
cactgacgaa tagtcttgct cc                                                  22

<210> SEQ ID NO 47
<211> LENGTH: 18
<212> TYPE: DNA
<213> ORGANISM: Artificial Sequence
<220> FEATURE:
<223> OTHER INFORMATION: primer

<400> SEQUENCE: 47
accaggccat ggatgaag                                                       18

<210> SEQ ID NO 48
<211> LENGTH: 20
<212> TYPE: DNA
<213> ORGANISM: Artificial Sequence
<220> FEATURE:
<223> OTHER INFORMATION: primer

<400> SEQUENCE: 48
ggttaagggg tcgttaattc                                                     20

<210> SEQ ID NO 49
<211> LENGTH: 21
<212> TYPE: DNA
<213> ORGANISM: Artificial Sequence
<220> FEATURE:
<223> OTHER INFORMATION: primer

<400> SEQUENCE: 49
ctcaccggat gcaccaatgt t                                                   21

<210> SEQ ID NO 50
<211> LENGTH: 21
<212> TYPE: DNA
<213> ORGANISM: Artificial Sequence
<220> FEATURE:

```
<223> OTHER INFORMATION: primer

<400> SEQUENCE: 50
tacttgtaac actcgttgcg c                                                        21
```